US007919300B2

(12) United States Patent
Wang et al.

(10) Patent No.: US 7,919,300 B2
(45) Date of Patent: Apr. 5, 2011

(54) GLUCOSE ISOMERASE MUTANTS

(76) Inventors: Jun Wang, Hong Kong (CN); Rongzhao Fu, Sunshine (CN); Dong Shen, Gansu (CN); Caike Jin, Zhuhai (CN); Zhangming Liu, Hong Kong (CN); Junming Chen, Guangdong (CN)

( * ) Notice: Subject to any disclaimer, the term of this patent is extended or adjusted under 35 U.S.C. 154(b) by 762 days.

(21) Appl. No.: 11/597,609

(22) PCT Filed: Jul. 28, 2004

(86) PCT No.: PCT/CN2004/000876
§ 371 (c)(1),
(2), (4) Date: Aug. 13, 2007

(87) PCT Pub. No.: WO2005/116217
PCT Pub. Date: Dec. 8, 2005

(65) Prior Publication Data
US 2008/0113415 A1    May 15, 2008

(30) Foreign Application Priority Data

May 26, 2004   (CN) .......................... 2004 1 0042773
Jun. 16, 2004   (CN) .......................... 2004 1 0047865

(51) Int. Cl.
*C12N 9/92* (2006.01)
*C12P 19/02* (2006.01)
*C07H 21/04* (2006.01)

(52) U.S. Cl. .......... 435/234; 435/105; 435/94; 536/23.2

(58) Field of Classification Search ........................ None
See application file for complete search history.

(56) References Cited

U.S. PATENT DOCUMENTS 5,384,257 A * 1/1995 Lambeir et al. ............... 435/234
5,656,497 A * 8/1997 Zeikus et al. ............. 435/320.1

FOREIGN PATENT DOCUMENTS
WO    WO-03/062387    *    7/2003

OTHER PUBLICATIONS

Lee et al., "Catalytic Mechanism of Xylose (Glucose) Isomerase from *Clostridium Thermosulfurogenes*". *J. of Biol.*, v.265(31): pp. 19082-19090, 1990.
Liu et al., "Purification and Cloning of a Thermostable Xylose (Glucose) Isomerase with an Acidic pH Optimum form *Thermoanaerobacterium* Strain JW/SL-YS 489". *J. of Bacteriol.*, v.178(20): pp. 5938-5945, 1996.

Kaneko et al., "Characterization of Acid-Stable Glucose Isomerase from *Streptomyces* sp., and Development of Single-Step Process for High-Fructose". *Biosci. Biotechnol. Biochem.*, v.64: pp. 940-947, 2000.
Lee et al., "Genetic Organization, Sequence and Biochemical Characterization of Recombinant β-xylosidase from *Thermoanaerobacterium saccharolyticum* Strain B6A-RI". *J. of Gen. Micro. Bio.*, v.139: pp. 1127-1234, 1993.
Vieille et al., "Xylose Isomerases from *Thermotoga*". *Methods of Enzymol.*, v. 330: pp. 215-224, 2001.
Lee et al., "Cloning, Sequencing and Biochemical Characterization of Xylose Isomerase from *Thermoanaerobacterium saccharolyticum* Strain B6A-RI". *J. of Gen. Microbiol.*, v.139: pp. 1241-1243, 1993.
Scriprapundh et al., "Molecular Determinants of Xylose Isomerase Thermal Stability and Activity: Analysis of Thermozymes by Site-Directed Mutagenesis". *Protein Engineering*, v. 13: pp. 259-265, 2000.
Scriprapundh et al., "Directed Evolution of *Thermatoga neapolitana* Xylose Isomerase: High Activity on Glucose at Low Temperature and Low pH". *Protein Engineering*, v.16: pp.683-690, 2003.
Lee et al., "Catalytic Mechanism of Xylose (Glucose) Isomerase from *Clostridium thermosulfurogenes*." *The Journal of Biological Chemistry*, v.265:31, pp. 19082-19090 (1990) .
Liu et al., "Purification and Cloning of a Thermostable Xylose (Glucose) Isomerase with an Acidic pH Optimum from *Thermoanaerobacterium* Strain JW/SL-YS 489." *Journal of Bacteriology*, v.178:20, pp. 5938-5945 (1996).
Meng et al., "Switching substrate preference of thermophilic xylose isomerase from D-xylose to D-glucose by redesigning the substrate." *Proc. Natl. Acad. Sci. USA*, v.88, pp. 4015-4019 (1991).
Meng et al., "The role of active-site aromatic and polar residues in catalysis and substrate discrimination by xylose isomerase." *Proc. Natl. Acad. Sci. USA*, v.90, pp. 8459-8463 (1993).
Lee et al., "Cloning, sequencing and biochemical characterization of yxlose isomerase from *Thermoanaerobacterium saccharolyticum* strain B6A-RI." *Journal of General Microbiology*, v.139, pp. 1227-1234 (1993).
Meaden et al., "The xylose isomerase-encoding gene (*xylA*) of *Clostridium thermosaccharolyticum*: cloning, sequencing and phylogeny of XylA enzymes." *Gene*, v.141, pp. 97-101 (1994).

* cited by examiner

*Primary Examiner* — Anand U Desai
*Assistant Examiner* — Iqbal H Chowdhury
(74) *Attorney, Agent, or Firm* — The Nath Law Group; Tanya E. Harkins; Ari G. Zytcer

(57) ABSTRACT

This invention describes a series of recombinant *Thermoanaerobacterium saccharolyticum* glucose isomerases having improved catalytic activity and thermostability. The recombinant glucose isomerases can be used for direct production of fructose syrup containing 55 wt % or higher concentration of fructose, or used for the production of fructose syrup containing less than 55 wt % fructose.

18 Claims, 3 Drawing Sheets

FIG. 1 The Polyacrylamide Gel Electrophoresis of Glucose Isomerase Mutant MGI-4.
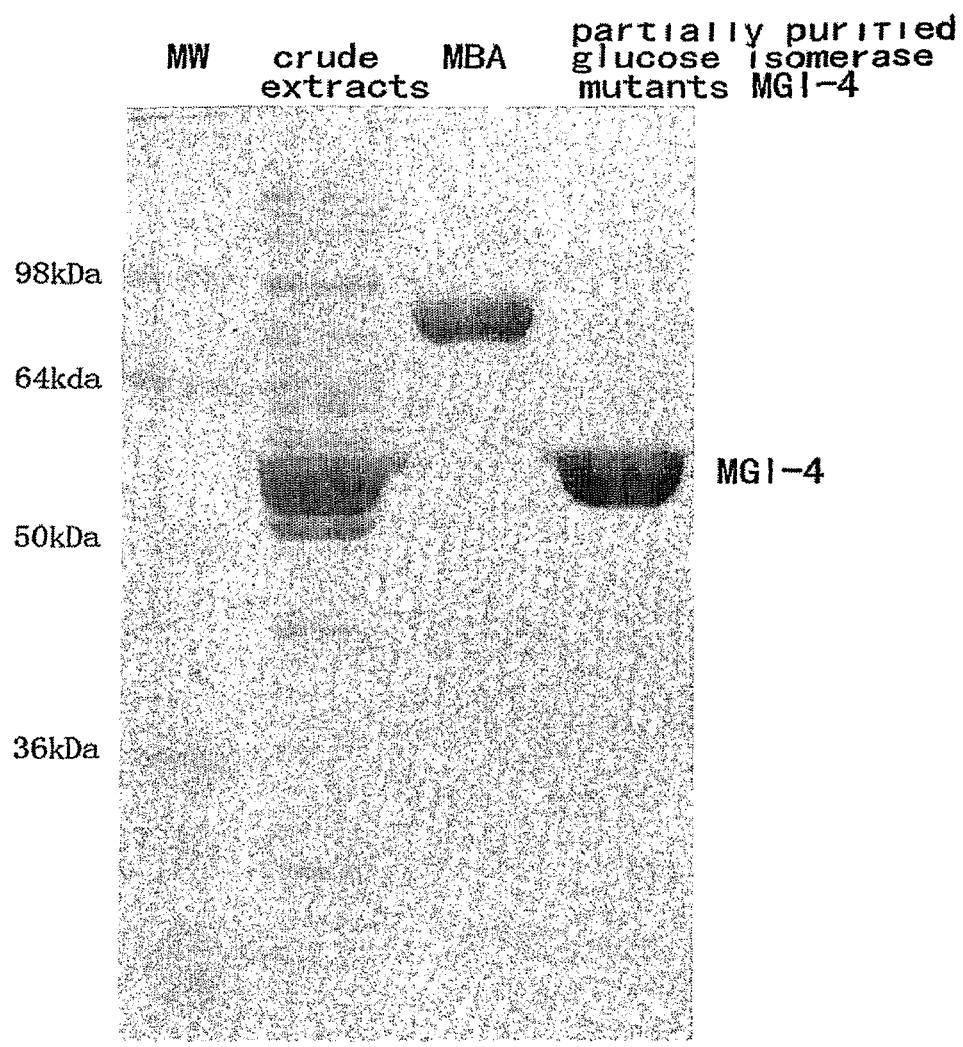

FIG. 2 Conversion of D-glucose to Fuctose by Glucose Isomerase Mutant MGI-4 at 80°C.
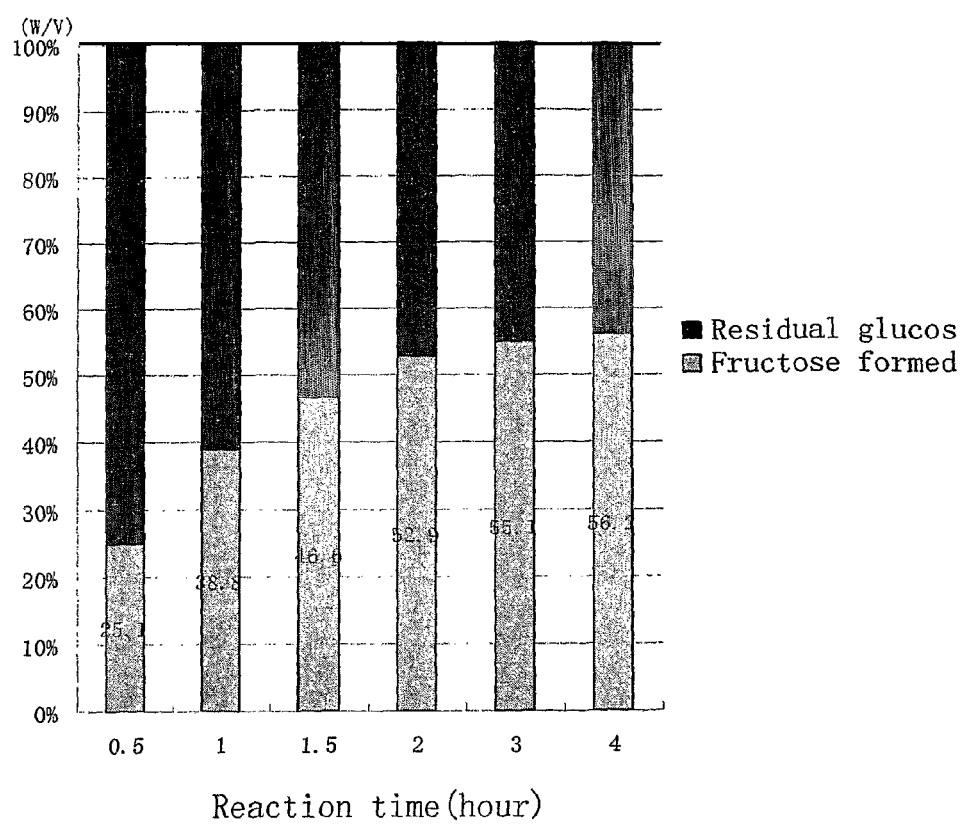

FIG. 3 The Thermal Stability of the Wild-type Glucose Isomerase and Glucose Isomerase Mutants.
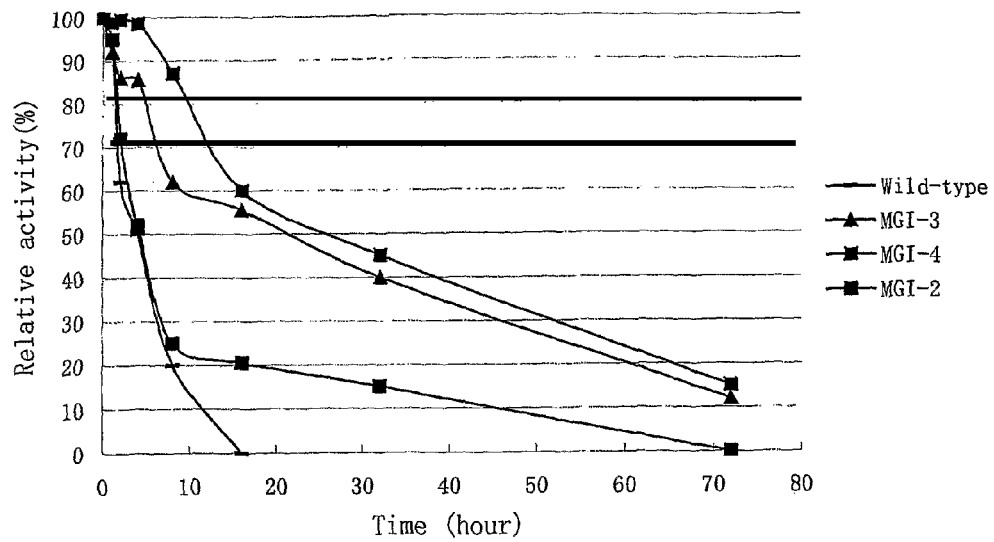
FIG. 4 The Effect of pH to the Wlid-type Glucose Isomerase and Glucose Isomerase Mutants.
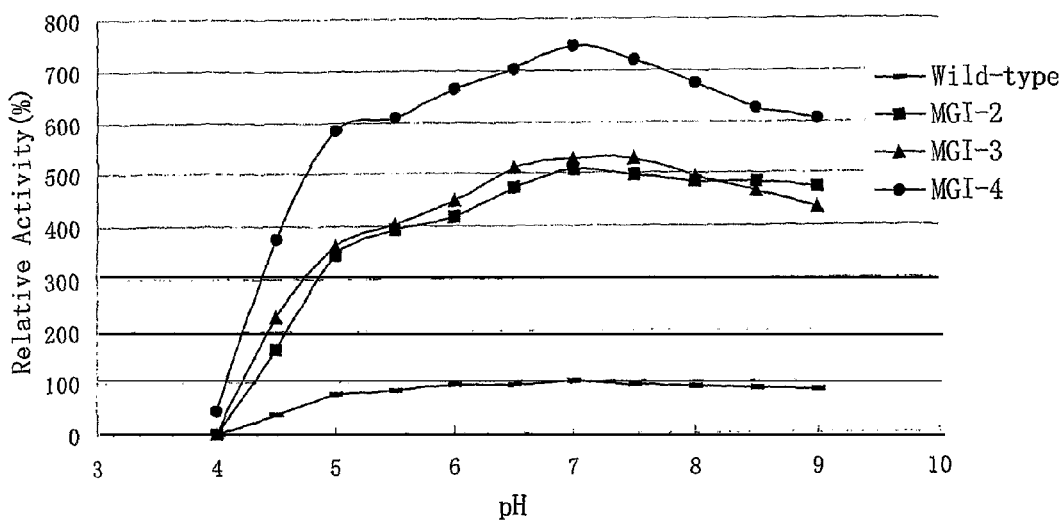

SEQUENCE LISTING

```
<160> NUMBER OF SEQ ID NOS: 80

<210> SEQ ID NO 1
<211> LENGTH: 1320
<212> TYPE: DNA
<213> ORGANISM: Thermoanaerobacterium saccharolyticum

<400> SEQUENCE: 1
atgaataaat attttgagaa cgtatctaaa ataaaatatg aaggaccaaa atcaaataat      60
ccttattcct ttaaatttta caatccagag gaagtaatcg atggcaagac gatggaggag     120
catctccgct tttctatagc ttattggcac acttttactg ctgatggaac agatcaattt     180
ggcaaggcta ctatgcaaag accatggaac cactacacag atcctatgga tatagcgaaa     240
gcaagggtag aagcagcatt tgagtttttt gataagataa atgcaccttt cttctgcttc     300
catgataggg atattgcccc tgaaggagat actcttagag agacaaacaa aaacttagat     360
acaatagttg ctatgataaa ggattactta aagaccagca agacaaaagt tttgtggggt     420
accgcaaatc ttttctccaa tccgagattt gtacatggtg catcaacatc ctgcaatgct     480 gacgttttg catattctgc agcgcaagtc aaaaaagccc ttgagattac taaggagctt     540
ggccgcgaaa actacgtatt ttggggtgga agagaagggt acgagacgct tctcaataca     600
gatatggagt tagagcttga taactttgca agatttttgc acatggctgt tgactatgca     660
aaggaaatcg gctttgaagg tcagttcttg attgagccga agccaaagga gcctacaaaa     720
catcaatacg actttgacgt ggcaaatgta ttggcattct tgagaaaata cgaccttgac     780
aaatatttca aagtaaatat cgaagcaaac catgcgacat tggcattcca cgacttccaa     840
catgagctaa gatacgccag aataaacggt gtattaggat caattgacgc aaatacaggc     900
```

```
gacatgcttt tgggatggga tacggaccag ttccctacag atatacgcat gacaacgctt    960
gctatgtatg aagtcataaa gatgggtgga tttgacaaag gtggccttaa ctttgatgca   1020
aaagtaagac gtgcttcatt tgagccagaa gatcttttct taggtcacat agcaggaatg   1080
gatgcttttg caaaaggctt taaagttgct tacaagcttg tgaaagatgg cgtatttgac   1140
aagttcatcg aagaaagata cgcaagctac aaagaaggca ttggcgctga tattgtaagc   1200
ggtaaagctg acttcaagag ccttgaaaag tatgcattag agcacagcca gattgtaaac   1260
aaatcaggca gacaagagct attagaatca atcctaaatc agtatttgtt tgcagaataa   1320
```

<210> SEQ ID NO 2
<211> LENGTH: 439
<212> TYPE: PRT
<213> ORGANISM: Thermoanaerobacterium saccharolyticum

<400> SEQUENCE: 2

```
Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
```

```
            305                 310                 315                 320
Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 3
<211> LENGTH: 1320
<212> TYPE: DNA
<213> ORGANISM: Thermoanaerobacterium saccharolyticum
<220> FEATURE:
<221> NAME/KEY: misc_feature
<222> LOCATION: (415)..(417)
<223> OTHER INFORMATION: "n" represents a,t,g or c; and "nnn" represents
      any other amino acid code except for typtophan.
<220> FEATURE:
<221> NAME/KEY: misc_feature
<222> LOCATION: (544)..(546)
<223> OTHER INFORMATION: "n" represents a,t,g or c; and "nnn" represents
      any other amino acid Arginine.
<220> FEATURE:
<221> NAME/KEY: misc_feature
<222> LOCATION: (559)..(561)
<223> OTHER INFORMATION: "n" represents a,t,g or c; and "nnn" represents
      any other amino acid code except for phenylalanine.
<220> FEATURE:
<221> NAME/KEY: misc_feature
<222> LOCATION: (895)..(897)
<223> OTHER INFORMATION: "n" represents a,t,g or c; and "nnn" represents
      any other amino acid code except for threonine.

<400> SEQUENCE: 3
atgaataaat attttgagaa cgtatctaaa ataaatatg aaggaccaaa atcaaataat      60
ccttattcct ttaaatttta caatccagag gaagtaatcg atggcaagac gatggaggag    120
catctccgct tttctatagc ttattggcac acttttactg ctgatggaac agatcaattt    180
ggcaaggcta ctatgcaaag accatggaac cactacacag atcctatgga tatagcgaaa    240
gcaagggtag aagcagcatt tgagtttttt gataagataa atgcaccttt cttctgcttc    300
catgataggg atattgcccc tgaaggagat actcttagag agacaaacaa aaacttagat    360
acaatagttg ctatgataaa ggattactta agaccagca agacaaaagt tttgnnnggt     420
accgcaaatc ttttctccaa tccgagattt gtacatggtg catcaacatc ctgcaatgct    480 gacgttttg catattctgc agcgcaagtc aaaaaagccc ttgagattac taaggagctt     540
ggcnnngaaa actacgtann ntgggctgga agagaagggt acgagacgct tctcaataca    600
gatatggagt tagagcttga taactttgca agattttttgc acatggctgt tgactatgca    660
aaggaaatcg gctttgaagg tcagttcttg attgagccga agccaaggga gcctacaaaa    720
catcaatacg actttgacgt ggcaaatgta ttggcattct tgagaaaata cgaccttgac    780
```

```
aaatatttca aagtaaatat cgaagcaaac catgcgacat tggcattcca cgacttccaa      840
catgagctaa gatacgccag aataaacggt gtattaggat caattgacgc aaatnnnggc      900
gacatgcttt tgggatggga tacggaccag ttccctacag atatacgcat gacaacgctt      960
gctatgtatg aagtcataaa gatgggtgga tttgacaaag gtggccttaa ctttgatgca     1020
aaagtaagac gtgcttcatt tgagccagaa gatctttct taggtcacat agcaggaatg     1080
gatgcttttg caaaaggctt taaagttgct tacaagcttg tgaaagatgg cgtatttgac     1140
aagttcatcg aagaaagata cgcaagctac aaagaaggca ttggcgctga tattgtaagc     1200
ggtaaagctg acttcaagag ccttgaaaag tatgcattag agcacagcca gattgtaaac     1260
aaatcaggca gacaagagct attagaatca atcctaaatc agtatttgtt tgcagaataa     1320
```

<210> SEQ ID NO 4
<211> LENGTH: 439
<212> TYPE: PRT
<213> ORGANISM: Thermoanaerobacterium saccharolyticum
<220> FEATURE:
<221> NAME/KEY: MISC_FEATURE
<222> LOCATION: (139)..(139)
<223> OTHER INFORMATION: Xaa represents any amino acid residue other
      than tryptophan.
<220> FEATURE:
<221> NAME/KEY: MISC_FEATURE
<222> LOCATION: (182)..(182)
<223> OTHER INFORMATION: Xaa represents any amino acid residue other
      than Arginine.
<220> FEATURE:
<221> NAME/KEY: MISC_FEATURE
<222> LOCATION: (187)..(187)
<223> OTHER INFORMATION: Xaa represents any amino acid residue other
      than phenylalanine.
<220> FEATURE:
<221> NAME/KEY: MISC_FEATURE
<222> LOCATION: (299)..(299)
<223> OTHER INFORMATION: Xaa represents any other amino acid residue
      other than threonine.

<400> SEQUENCE: 4

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Xaa Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Xaa Glu Asn Tyr Val Xaa Trp Gly Gly Arg Glu

```
                    180                 185                 190
Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Xaa Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Ser Ile Leu
            420                 425                 430

Asn Gln Tyr Leu Phe Ala Glu
        435

<210> SEQ ID NO 5
<211> LENGTH: 439
<212> TYPE: PRT
<213> ORGANISM: Thermoanaerobacterium saccharolyticum

<400> SEQUENCE: 5

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
```

```
                115                 120                 125
Tyr Leu Lys Thr Ser Lys Thr Lys Val Leu Phe Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 6
<211> LENGTH: 439
<212> TYPE: PRT
<213> ORGANISM: Thermoanaerobacterium saccharolyticum

<400> SEQUENCE: 6

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
```

```
               50                  55                  60
Met Gln Arg Pro Trp Asn His Tyr Thr Asp Pro Met Asp Ile Ala Lys
 65                  70                  75                  80

Ala Arg Val Glu Ala Ala Phe Glu Phe Phe Asp Lys Ile Asn Ala Pro
                     85                  90                  95

Phe Phe Cys Phe His Asp Arg Asp Ile Ala Pro Glu Gly Asp Thr Leu
                    100                 105                 110

Arg Glu Thr Asn Lys Asn Leu Asp Thr Ile Val Ala Met Ile Lys Asp
                    115                 120                 125

Tyr Leu Lys Thr Ser Lys Thr Lys Val Leu Lys Gly Thr Ala Asn Leu
                    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                    165                 170                 175

Thr Lys Glu Leu Gly Arg Glu Asn Tyr Val Phe Trp Gly Gly Arg Glu
                    180                 185                 190

Gly Tyr Glu Thr Leu Leu Asn Thr Asp Met Glu Leu Glu Leu Asp Asn
                    195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                    245                 250                 255

Tyr Asp Leu Asp Lys Tyr Phe Lys Val Asn Ile Glu Ala Asn His Ala
                    260                 265                 270

Thr Leu Ala Phe His Asp Phe Gln His Glu Leu Arg Tyr Ala Arg Ile
                    275                 280                 285

Asn Gly Val Leu Gly Ser Ile Asp Ala Asn Thr Gly Asp Met Leu Leu
                    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                    325                 330                 335

Asn Phe Asp Ala Lys Val Arg Arg Ala Ser Phe Glu Pro Glu Asp Leu
                    340                 345                 350

Phe Leu Gly His Ile Ala Gly Met Asp Ala Phe Ala Lys Gly Phe Lys
                    355                 360                 365

Val Ala Tyr Lys Leu Val Lys Asp Gly Val Phe Asp Lys Phe Ile Glu
                    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                    405                 410                 415

Gln Ile Val Asn Lys Ser Gly Arg Gln Glu Leu Leu Glu Ser Ile Leu
                    420                 425                 430

Asn Gln Tyr Leu Phe Ala Glu
            435

<210> SEQ ID NO 7
<211> LENGTH: 439
<212> TYPE: PRT
<213> ORGANISM: Thermoanaerobacterium saccharolyticum
```

-continued

<400> SEQUENCE: 7

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Ser Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

-continued

```
Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 8
<211> LENGTH: 439
<212> TYPE: PRT
<213> ORGANISM: Thermoanaerobacterium saccharolyticum

<400> SEQUENCE: 8

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Cys Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350
```

```
Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 9
<211> LENGTH: 439
<212> TYPE: PRT
<213> ORGANISM: Thermoanaerobacterium saccharolyticum

<400> SEQUENCE: 9

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Ile Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285
```

```
Asn Gly Val Leu Gly Ser Ile Asp Ala Asn Thr Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 10
<211> LENGTH: 439
<212> TYPE: PRT
<213> ORGANISM: Thermoanaerobacterium saccharolyticum

<400> SEQUENCE: 10

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Thr Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220
```

```
Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
        260                 265                 270

Thr Leu Ala Phe His Asp Phe Gln His Glu Leu Arg Tyr Ala Arg Ile
    275                 280                 285

Asn Gly Val Leu Gly Ser Ile Asp Ala Asn Thr Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
    355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Ser Ile Leu
        420                 425                 430

Asn Gln Tyr Leu Phe Ala Glu
            435

<210> SEQ ID NO 11
<211> LENGTH: 439
<212> TYPE: PRT
<213> ORGANISM: Thermoanaerobacterium saccharolyticum

<400> SEQUENCE: 11

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
            85                  90                  95

Phe Phe Cys Phe His Asp Arg Asp Ile Ala Pro Glu Gly Asp Thr Leu
        100                 105                 110

Arg Glu Thr Asn Lys Asn Leu Asp Thr Ile Val Ala Met Ile Lys Asp
    115                 120                 125

Tyr Leu Lys Thr Ser Lys Thr Lys Val Leu Asn Gly Thr Ala Asn Leu
130                 135                 140

Phe Ser Asn Pro Arg Phe Val His Gly Ala Ser Thr Ser Cys Asn Ala
145                 150                 155                 160
```

```
Asp Val Phe Ala Tyr Ser Ala Ala Gln Val Lys Lys Ala Leu Glu Ile
            165                 170                 175

Thr Lys Glu Leu Gly Arg Glu Asn Tyr Val Phe Trp Gly Gly Arg Glu
        180                 185                 190

Gly Tyr Glu Thr Leu Leu Asn Thr Asp Met Glu Leu Glu Leu Asp Asn
    195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
        260                 265                 270

Thr Leu Ala Phe His Asp Phe Gln His Glu Leu Arg Tyr Ala Arg Ile
    275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
    355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Ser Ile Leu
        420                 425                 430

Asn Gln Tyr Leu Phe Ala Glu
        435

<210> SEQ ID NO 12
<211> LENGTH: 439
<212> TYPE: PRT
<213> ORGANISM: Thermoanaerobacterium saccharolyticum

<400> SEQUENCE: 12

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
            85                  90                  95
```

```
Phe Phe Cys Phe His Asp Arg Asp Ile Ala Pro Gly Asp Thr Leu
                100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Trp Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
                210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 13
<211> LENGTH: 439
<212> TYPE: PRT
<213> ORGANISM: Thermoanaerobacterium saccharolyticum

<400> SEQUENCE: 13

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30
```

```
Ile Asp Gly Lys Thr Met Glu Glu His Leu Arg Phe Ser Ile Ala Tyr
     35                  40                  45

Trp His Thr Phe Thr Ala Asp Gly Thr Asp Gln Phe Gly Lys Ala Thr
 50                  55                  60

Met Gln Arg Pro Trp Asn His Tyr Thr Asp Pro Met Asp Ile Ala Lys
 65                  70                  75                  80

Ala Arg Val Glu Ala Ala Phe Glu Phe Phe Asp Lys Ile Asn Ala Pro
                 85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Trp Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Pro Glu Asn Tyr Val Phe Trp Gly Gly Arg Glu
            180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 14
```

```
<211> LENGTH: 439
<212> TYPE: PRT
<213> ORGANISM: Thermoanaerobacterium saccharolyticum

<400> SEQUENCE: 14
```

| | | | | | | | | | | | | | | |
|---|---|---|---|---|---|---|---|---|---|---|---|---|---|---|
| Met | Asn | Lys | Tyr | Phe | Glu | Asn | Val | Ser | Lys | Ile | Lys | Tyr | Gly | Pro |
| 1 | | | | 5 | | | | | 10 | | | | | 15 |

Lys Ser Asn Asn Pro Tyr Ser Phe Lys Phe Tyr Asn Pro Glu Glu Val
             20                  25                  30

Ile Asp Gly Lys Thr Met Glu Glu His Leu Arg Phe Ser Ile Ala Tyr
         35                  40                  45

Trp His Thr Phe Thr Ala Asp Gly Thr Asp Gln Phe Gly Lys Ala Thr
     50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                 85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ser Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

-continued

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 15
<211> LENGTH: 439
<212> TYPE: PRT
<213> ORGANISM: Thermoanaerobacterium saccharolyticum

<400> SEQUENCE: 15

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Trp Gly Thr Ala Asn Leu
            130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ile Glu Asn Tyr Val Phe Trp Gly Gly Arg Glu
            180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
            210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
            275                 280                 285

Asn Gly Val Leu Gly Ser Ile Asp Ala Asn Thr Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

```
Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 16
<211> LENGTH: 439
<212> TYPE: PRT
<213> ORGANISM: Thermoanaerobacterium saccharolyticum

<400> SEQUENCE: 16

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Thr Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270
```

```
Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
        435

<210> SEQ ID NO 17
<211> LENGTH: 439
<212> TYPE: PRT
<213> ORGANISM: Thermoanaerobacterium saccharolyticum

<400> SEQUENCE: 17

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Val Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205
```

```
Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Ser Ile Leu
            420                 425                 430

Asn Gln Tyr Leu Phe Ala Glu
        435

<210> SEQ ID NO 18
<211> LENGTH: 439
<212> TYPE: PRT
<213> ORGANISM: Thermoanaerobacterium saccharolyticum

<400> SEQUENCE: 18

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140
```

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
            165                 170                 175

Thr Lys Glu Leu Gly Arg Glu Asn Tyr Val Ser Trp Gly Gly Arg Glu
        180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
        260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Ser Ile Leu
        420                 425                 430

Asn Gln Tyr Leu Phe Ala Glu
        435

<210> SEQ ID NO 19
<211> LENGTH: 439
<212> TYPE: PRT
<213> ORGANISM: Thermoanaerobacterium saccharolyticum

<400> SEQUENCE: 19

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

```
Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Gly Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 20
<211> LENGTH: 439
<212> TYPE: PRT
<213> ORGANISM: Thermoanaerobacterium saccharolyticum

<400> SEQUENCE: 20

Met Asn Lys Tyr Phe Glu Asn Val Ser Lys Ile Lys Tyr Glu Gly Pro
1               5                   10                  15
```

```
Lys Ser Asn Asn Pro Tyr Ser Phe Lys Phe Tyr Asn Pro Glu Glu Val
             20                  25                  30
Ile Asp Gly Lys Thr Met Glu Glu His Leu Arg Phe Ser Ile Ala Tyr
         35                  40                  45
Trp His Thr Phe Thr Ala Asp Gly Thr Asp Gln Phe Gly Lys Ala Thr
     50                  55                  60
Met Gln Arg Pro Trp Asn His Tyr Thr Asp Pro Met Asp Ile Ala Lys
 65                  70                  75                  80
Ala Arg Val Glu Ala Ala Phe Glu Phe Phe Asp Lys Ile Asn Ala Pro
                 85                  90                  95
Phe Phe Cys Phe His Asp Arg Asp Ile Ala Pro Glu Gly Asp Thr Leu
             100                 105                 110
Arg Glu Thr Asn Lys Asn Leu Asp Thr Ile Val Ala Met Ile Lys Asp
         115                 120                 125
Tyr Leu Lys Thr Ser Lys Thr Lys Val Leu Trp Gly Thr Ala Asn Leu
     130                 135                 140
Phe Ser Asn Pro Arg Phe Val His Gly Ala Ser Thr Ser Cys Asn Ala
145                 150                 155                 160
Asp Val Phe Ala Tyr Ser Ala Ala Gln Val Lys Lys Ala Leu Glu Ile
                 165                 170                 175
Thr Lys Glu Leu Gly Arg Glu Asn Tyr Val Pro Trp Gly Gly Arg Glu
         180                 185                 190
Gly Tyr Glu Thr Leu Leu Asn Thr Asp Met Glu Leu Glu Leu Asp Asn
     195                 200                 205
Phe Ala Arg Phe Leu His Met Ala Val Asp Tyr Ala Lys Glu Ile Gly
210                 215                 220
Phe Glu Gly Gln Phe Leu Ile Glu Pro Lys Pro Lys Glu Pro Thr Lys
225                 230                 235                 240
His Gln Tyr Asp Phe Asp Val Ala Asn Val Leu Ala Phe Leu Arg Lys
                 245                 250                 255
Tyr Asp Leu Asp Lys Tyr Phe Lys Val Asn Ile Glu Ala Asn His Ala
         260                 265                 270
Thr Leu Ala Phe His Asp Phe Gln His Glu Leu Arg Tyr Ala Arg Ile
     275                 280                 285
Asn Gly Val Leu Gly Ser Ile Asp Ala Asn Thr Gly Asp Met Leu Leu
290                 295                 300
Gly Trp Asp Thr Asp Gln Phe Pro Thr Asp Ile Arg Met Thr Thr Leu
305                 310                 315                 320
Ala Met Tyr Glu Val Ile Lys Met Gly Gly Phe Asp Lys Gly Gly Leu
                 325                 330                 335
Asn Phe Asp Ala Lys Val Arg Arg Ala Ser Phe Glu Pro Glu Asp Leu
         340                 345                 350
Phe Leu Gly His Ile Ala Gly Met Asp Ala Phe Ala Lys Gly Phe Lys
     355                 360                 365
Val Ala Tyr Lys Leu Val Lys Asp Gly Val Phe Asp Lys Phe Ile Glu
     370                 375                 380
Glu Arg Tyr Ala Ser Tyr Lys Glu Gly Ile Gly Ala Asp Ile Val Ser
385                 390                 395                 400
Gly Lys Ala Asp Phe Lys Ser Leu Glu Lys Tyr Ala Leu Glu His Ser
                 405                 410                 415
Gln Ile Val Asn Lys Ser Gly Arg Gln Glu Leu Leu Glu Ser Ile Leu
         420                 425                 430
Asn Gln Tyr Leu Phe Ala Glu
```

435

<210> SEQ ID NO 21
<211> LENGTH: 439
<212> TYPE: PRT
<213> ORGANISM: Thermoanaerobacterium saccharolyticum

<400> SEQUENCE: 21

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Ala Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu

```
                370             375             380
Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
                435

<210> SEQ ID NO 22
<211> LENGTH: 439
<212> TYPE: PRT
<213> ORGANISM: Thermoanaerobacterium saccharolyticum

<400> SEQUENCE: 22

Met Asn Lys Tyr Phe Glu Asn Val Ser Lys Ile Lys Tyr Gly Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
```

```
              305                 310                 315                 320
         Ala Met Tyr Glu Val Ile Lys Met Gly Gly Phe Asp Lys Gly Gly Leu
                         325                 330                 335

Asn Phe Asp Ala Lys Val Arg Arg Ala Ser Phe Glu Pro Glu Asp Leu
                         340                 345                 350

Phe Leu Gly His Ile Ala Gly Met Asp Ala Phe Ala Lys Gly Phe Lys
                         355                 360                 365

Val Ala Tyr Lys Leu Val Lys Asp Gly Val Phe Asp Lys Phe Ile Glu
                         370                 375                 380

Glu Arg Tyr Ala Ser Tyr Lys Glu Gly Ile Gly Ala Asp Ile Val Ser
         385                 390                 395                 400

Gly Lys Ala Asp Phe Lys Ser Leu Glu Lys Tyr Ala Leu Glu His Ser
                         405                 410                 415

Gln Ile Val Asn Lys Ser Gly Arg Gln Glu Leu Leu Glu Ser Ile Leu
                         420                 425                 430

Asn Gln Tyr Leu Phe Ala Glu
                         435

<210> SEQ ID NO 23
<211> LENGTH: 439
<212> TYPE: PRT
<213> ORGANISM: Thermoanaerobacterium saccharolyticum

<400> SEQUENCE: 23

Met Asn Lys Tyr Phe Glu Asn Val Ser Lys Ile Lys Tyr Glu Gly Pro
         1               5                   10                  15

Lys Ser Asn Asn Pro Tyr Ser Phe Lys Phe Tyr Asn Pro Glu Glu Val
                         20                  25                  30

Ile Asp Gly Lys Thr Met Glu Glu His Leu Arg Phe Ser Ile Ala Tyr
                         35                  40                  45

Trp His Thr Phe Thr Ala Asp Gly Thr Asp Gln Phe Gly Lys Ala Thr
                         50                  55                  60

Met Gln Arg Pro Trp Asn His Tyr Thr Asp Pro Met Asp Ile Ala Lys
         65                  70                  75                  80

Ala Arg Val Glu Ala Ala Phe Glu Phe Phe Asp Lys Ile Asn Ala Pro
                         85                  90                  95

Phe Phe Cys Phe His Asp Arg Asp Ile Ala Pro Glu Gly Asp Thr Leu
                         100                 105                 110

Arg Glu Thr Asn Lys Asn Leu Asp Thr Ile Val Ala Met Ile Lys Asp
                         115                 120                 125

Tyr Leu Lys Thr Ser Lys Thr Lys Val Leu Trp Gly Thr Ala Asn Leu
                         130                 135                 140

Phe Ser Asn Pro Arg Phe Val His Gly Ala Ser Thr Ser Cys Asn Ala
         145                 150                 155                 160

Asp Val Phe Ala Tyr Ser Ala Ala Gln Val Lys Lys Ala Leu Glu Ile
                         165                 170                 175

Thr Lys Glu Leu Gly Arg Glu Asn Tyr Val Phe Trp Gly Gly Arg Glu
                         180                 185                 190

Gly Tyr Glu Thr Leu Leu Asn Thr Asp Met Glu Leu Glu Leu Asp Asn
                         195                 200                 205

Phe Ala Arg Phe Leu His Met Ala Val Asp Tyr Ala Lys Glu Ile Gly
                         210                 215                 220

Phe Glu Gly Gln Phe Leu Ile Glu Pro Lys Pro Lys Glu Pro Thr Lys
         225                 230                 235                 240

His Gln Tyr Asp Phe Asp Val Ala Asn Val Leu Ala Phe Leu Arg Lys
```

```
                       245                 250                 255
Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Ile Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
    355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Glu Ser Ile Leu
        420                 425                 430

Asn Gln Tyr Leu Phe Ala Glu
            435

<210> SEQ ID NO 24
<211> LENGTH: 439
<212> TYPE: PRT
<213> ORGANISM: Thermoanaerobacterium saccharolyticum

<400> SEQUENCE: 24

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
            85                  90                  95

Phe Phe Cys Phe His Asp Arg Asp Ile Ala Pro Glu Gly Asp Thr Leu
        100                 105                 110

Arg Glu Thr Asn Lys Asn Leu Asp Thr Ile Val Ala Met Ile Lys Asp
    115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
            165                 170                 175

Thr Lys Glu Leu Gly Arg Glu Asn Tyr Val Phe Trp Gly Gly Arg Glu
```

```
                    180                 185                 190
Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
            210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
            275                 280                 285

Asn Gly Val Leu Gly Ser Ile Asp Ala Asn Tyr Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
            370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Ser Ile Leu
            420                 425                 430

Asn Gln Tyr Leu Phe Ala Glu
            435

<210> SEQ ID NO 25
<211> LENGTH: 439
<212> TYPE: PRT
<213> ORGANISM: Thermoanaerobacterium saccharolyticum

<400> SEQUENCE: 25

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
```

```
                115                 120                 125
Tyr Leu Lys Thr Ser Lys Thr Lys Val Leu Trp Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Cys Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 26
<211> LENGTH: 439
<212> TYPE: PRT
<213> ORGANISM: Thermoanaerobacterium saccharolyticum

<400> SEQUENCE: 26

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
```

```
                50                  55                  60
Met Gln Arg Pro Trp Asn His Tyr Thr Asp Pro Met Asp Ile Ala Lys
 65                  70                  75                  80

Ala Arg Val Glu Ala Ala Phe Glu Phe Phe Asp Lys Ile Asn Ala Pro
                 85                  90                  95

Phe Phe Cys Phe His Asp Arg Asp Ile Ala Pro Glu Gly Asp Thr Leu
                100                 105                 110

Arg Glu Thr Asn Lys Asn Leu Asp Thr Ile Val Ala Met Ile Lys Asp
                115                 120                 125

Tyr Leu Lys Thr Ser Lys Thr Lys Val Leu Trp Gly Thr Ala Asn Leu
                130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
                180                 185                 190

Gly Tyr Glu Thr Leu Leu Asn Thr Asp Met Glu Leu Glu Leu Asp Asn
                195                 200                 205

Phe Ala Arg Phe Leu His Met Ala Val Asp Tyr Ala Lys Glu Ile Gly
                210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
                260                 265                 270

Thr Leu Ala Phe His Asp Phe Gln His Glu Leu Arg Tyr Ala Arg Ile
                275                 280                 285

Asn Gly Val Leu Gly Ser Ile Asp Ala Asn Met Gly Asp Met Leu Leu
                290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
                355                 360                 365

Val Ala Tyr Lys Leu Val Lys Asp Gly Val Phe Asp Lys Phe Ile Glu
                370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
                435

<210> SEQ ID NO 27
<211> LENGTH: 439
<212> TYPE: PRT
<213> ORGANISM: Thermoanaerobacterium saccharolyticum
```

```
<400> SEQUENCE: 27

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415
```

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 28
<211> LENGTH: 439
<212> TYPE: PRT
<213> ORGANISM: Thermoanaerobacterium saccharolyticum

<400> SEQUENCE: 28

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

```
Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
                420                 425                 430

Asn Gln Tyr Leu Phe Ala Glu
            435

<210> SEQ ID NO 29
<211> LENGTH: 439
<212> TYPE: PRT
<213> ORGANISM: Thermoanaerobacterium saccharolyticum

<400> SEQUENCE: 29

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
                20                  25                  30

Ile Asp Gly Lys Thr Met Glu His Leu Arg Phe Ser Ile Ala Tyr
            35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Trp Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285
```

```
Asn Gly Val Leu Gly Ser Ile Asp Ala Asn Gln Gly Asp Met Leu Leu
        290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
                340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
            435

<210> SEQ ID NO 30
<211> LENGTH: 439
<212> TYPE: PRT
<213> ORGANISM: Thermoanaerobacterium saccharolyticum

<400> SEQUENCE: 30

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Phe Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Arg Glu Asn Tyr Val Phe Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220
```

```
Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
        260                 265                 270

Thr Leu Ala Phe His Asp Phe Gln His Glu Leu Arg Tyr Ala Arg Ile
    275                 280                 285

Asn Gly Val Leu Gly Ser Ile Asp Ala Asn Gln Gly Asp Met Leu Leu
290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
        340                 345                 350

Phe Leu Gly His Ile Ala Gly Met Asp Ala Phe Ala Lys Gly Phe Lys
    355                 360                 365

Val Ala Tyr Lys Leu Val Lys Asp Gly Val Phe Asp Lys Phe Ile Glu
370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Ser Ile Leu
        420                 425                 430

Asn Gln Tyr Leu Phe Ala Glu
        435

<210> SEQ ID NO 31
<211> LENGTH: 439
<212> TYPE: PRT
<213> ORGANISM: Thermoanaerobacterium saccharolyticum

<400> SEQUENCE: 31

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
            85                  90                  95

Phe Phe Cys Phe His Asp Arg Asp Ile Ala Pro Glu Gly Asp Thr Leu
        100                 105                 110

Arg Glu Thr Asn Lys Asn Leu Asp Thr Ile Val Ala Met Ile Lys Asp
    115                 120                 125

Tyr Leu Lys Thr Ser Lys Thr Lys Val Leu Phe Gly Thr Ala Asn Leu
130                 135                 140

Phe Ser Asn Pro Arg Phe Val His Gly Ala Ser Thr Ser Cys Asn Ala
145                 150                 155                 160
```

```
Asp Val Phe Ala Tyr Ser Ala Ala Gln Val Lys Lys Ala Leu Glu Ile
            165                 170                 175

Thr Lys Glu Leu Gly Ala Glu Asn Tyr Val Phe Trp Gly Gly Arg Glu
        180                 185                 190

Gly Tyr Glu Thr Leu Leu Asn Thr Asp Met Glu Leu Glu Leu Asp Asn
            195                 200                 205

Phe Ala Arg Phe Leu His Met Ala Val Asp Tyr Ala Lys Glu Ile Gly
        210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
            245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
            275                 280                 285

Asn Gly Val Leu Gly Ser Ile Asp Ala Asn Gln Gly Asp Met Leu Leu
            290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
            325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
            355                 360                 365

Val Ala Tyr Lys Leu Val Lys Asp Gly Val Phe Asp Lys Phe Ile Glu
        370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
            405                 410                 415

Gln Ile Val Asn Lys Ser Gly Arg Gln Glu Leu Leu Ser Ile Leu
            420                 425                 430

Asn Gln Tyr Leu Phe Ala Glu
            435

<210> SEQ ID NO 32
<211> LENGTH: 439
<212> TYPE: PRT
<213> ORGANISM: Thermoanaerobacterium saccharolyticum

<400> SEQUENCE: 32

Met Asn Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
        35                  40                  45

Trp His Thr Phe Thr Ala Asp Gly Thr Asp Gln Phe Gly Lys Ala Thr
    50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
            85                  90                  95
```

-continued

Phe Phe Cys Phe His Asp Arg Asp Ile Ala Pro Gly Asp Thr Leu
            100                 105                 110

Arg Glu Thr Asn Lys Asn Leu Asp Thr Ile Val Ala Met Ile Lys Asp
        115                 120                 125

Tyr Leu Lys Thr Ser Lys Thr Lys Val Leu Phe Gly Thr Ala Asn Leu
    130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Ala Glu Asn Tyr Val Ser Trp Gly Gly Arg Glu
            180                 185                 190

Gly Tyr Glu Thr Leu Leu Asn Thr Asp Met Glu Leu Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Gln Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Gly Val Phe Asp Lys Phe Ile Glu
    370                 375                 380

Glu Arg Tyr Ala Ser Tyr Lys Glu Gly Ile Gly Ala Asp Ile Val Ser
385                 390                 395                 400

Gly Lys Ala Asp Phe Lys Ser Leu Glu Lys Tyr Ala Leu Glu His Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 33
<211> LENGTH: 56
<212> TYPE: DNA
<213> ORGANISM: Artificial Sequence
<220> FEATURE:
<223> OTHER INFORMATION: synthetic primer

<400> SEQUENCE: 33
agcctaggtt aattaacttt aagaaggaga tatacatatg aataaatatt ttgaga        56

<210> SEQ ID NO 34

```
<211> LENGTH: 38
<212> TYPE: DNA
<213> ORGANISM: Artificial Sequence
<220> FEATURE:
<223> OTHER INFORMATION: synthetic primer

<400> SEQUENCE: 34
ataagctcag cggcgcgcct tattctgcaa acaaatac                              38

<210> SEQ ID NO 35
<211> LENGTH: 30
<212> TYPE: DNA
<213> ORGANISM: Artificial Sequence
<220> FEATURE:
<223> OTHER INFORMATION: synthetic primer

<400> SEQUENCE: 35
aagttttgaa aggtaccgca aatcttttct                                      30

<210> SEQ ID NO 36
<211> LENGTH: 30
<212> TYPE: DNA
<213> ORGANISM: Artificial Sequence
<220> FEATURE:
<223> OTHER INFORMATION: synthetic primer

<400> SEQUENCE: 36
tgcggtacct ttcaaaactt ttgtcttgct                                      30

<210> SEQ ID NO 37
<211> LENGTH: 30
<212> TYPE: DNA
<213> ORGANISM: Artificial Sequence
<220> FEATURE:
<223> OTHER INFORMATION: synthetic primer

<400> SEQUENCE: 37
aagttttgtc aggtaccgca aatcttttct                                      30

<210> SEQ ID NO 38
<211> LENGTH: 30
<212> TYPE: DNA
<213> ORGANISM: Artificial Sequence
<220> FEATURE:
<223> OTHER INFORMATION: synthetic primer

<400> SEQUENCE: 38
tgcggtacct gacaaaactt ttgtcttgct                                      30

<210> SEQ ID NO 39
<211> LENGTH: 30
<212> TYPE: DNA
<213> ORGANISM: Artificial Sequence
<220> FEATURE:
<223> OTHER INFORMATION: synthetic primer

<400> SEQUENCE: 39
aagttttgtg cggtaccgca aatcttttct                                      30

<210> SEQ ID NO 40
<211> LENGTH: 30
<212> TYPE: DNA
<213> ORGANISM: Artificial Sequence
<220> FEATURE:
<223> OTHER INFORMATION: synthetic primer

<400> SEQUENCE: 40
```
tgcggtaccg cacaaaactt ttgtcttgct                                              30

<210> SEQ ID NO 41
<211> LENGTH: 30
<212> TYPE: DNA
<213> ORGANISM: Artificial Sequence
<220> FEATURE:
<223> OTHER INFORMATION: synthetic primer

<400> SEQUENCE: 41
aagttttgat tggtaccgca aatcttttct                                              30

<210> SEQ ID NO 42
<211> LENGTH: 30
<212> TYPE: DNA
<213> ORGANISM: Artificial Sequence
<220> FEATURE:
<223> OTHER INFORMATION: synthetic primer

<400> SEQUENCE: 42
tgcggtacca atcaaaactt ttgtcttgct                                              30

<210> SEQ ID NO 43
<211> LENGTH: 30
<212> TYPE: DNA
<213> ORGANISM: Artificial Sequence
<220> FEATURE:
<223> OTHER INFORMATION: synthetic primer

<400> SEQUENCE: 43
aagttttgac aggtaccgca aatcttttct                                              30

<210> SEQ ID NO 44
<211> LENGTH: 30
<212> TYPE: DNA
<213> ORGANISM: Artificial Sequence
<220> FEATURE:
<223> OTHER INFORMATION: synthetic primer

<400> SEQUENCE: 44
tgcggtacct gtcaaaactt ttgtcttgct                                              30

<210> SEQ ID NO 45
<211> LENGTH: 30
<212> TYPE: DNA
<213> ORGANISM: Artificial Sequence
<220> FEATURE:
<223> OTHER INFORMATION: synthetic primer

<400> SEQUENCE: 45
aagttttgaa cggtaccgca aatcttttct                                              30

<210> SEQ ID NO 46
<211> LENGTH: 30
<212> TYPE: DNA
<213> ORGANISM: Artificial Sequence
<220> FEATURE:
<223> OTHER INFORMATION: synthetic primer

<400> SEQUENCE: 46
tgcggtaccg ttcaaaactt ttgtcttgct                                              30

<210> SEQ ID NO 47
<211> LENGTH: 33
<212> TYPE: DNA
<213> ORGANISM: Artificial Sequence
<220> FEATURE:

<223> OTHER INFORMATION: synthetic primer

<400> SEQUENCE: 47
aaaagttttg tttggtaccg caaatctttt ctc                33

<210> SEQ ID NO 48
<211> LENGTH: 33
<212> TYPE: DNA
<213> ORGANISM: Artificial Sequence
<220> FEATURE:
<223> OTHER INFORMATION: synthetic primer

<400> SEQUENCE: 48
ttgcggtacc aaacaaaact tttgtcttgc tgg                33

<210> SEQ ID NO 49
<211> LENGTH: 30
<212> TYPE: DNA
<213> ORGANISM: Artificial Sequence
<220> FEATURE:
<223> OTHER INFORMATION: synthetic primer

<400> SEQUENCE: 49
agcttggccc ggaaaactac gtattttggg                    30

<210> SEQ ID NO 50
<211> LENGTH: 30
<212> TYPE: DNA
<213> ORGANISM: Artificial Sequence
<220> FEATURE:
<223> OTHER INFORMATION: synthetic primer

<400> SEQUENCE: 50
gtagttttcc gggccaagct ccttagtaat                    30

<210> SEQ ID NO 51
<211> LENGTH: 30
<212> TYPE: DNA
<213> ORGANISM: Artificial Sequence
<220> FEATURE:
<223> OTHER INFORMATION: synthetic primer

<400> SEQUENCE: 51
agcttggctc agaaaactac gtattttggg                    30

<210> SEQ ID NO 52
<211> LENGTH: 30
<212> TYPE: DNA
<213> ORGANISM: Artificial Sequence
<220> FEATURE:
<223> OTHER INFORMATION: synthetic primer

<400> SEQUENCE: 52
gtagttttct gagccaagct ccttagtaat                    30

<210> SEQ ID NO 53
<211> LENGTH: 33
<212> TYPE: DNA
<213> ORGANISM: Artificial Sequence
<220> FEATURE:
<223> OTHER INFORMATION: synthetic primer

<400> SEQUENCE: 53
ggagcttggc gcggaaaact acgtattttg ggg                33

<210> SEQ ID NO 54

```
<211> LENGTH: 33
<212> TYPE: DNA
<213> ORGANISM: Artificial Sequence
<220> FEATURE:
<223> OTHER INFORMATION: synthetic primer

<400> SEQUENCE: 54
cgtagttttc cgcgccaagc tccttagtaa tct                              33

<210> SEQ ID NO 55
<211> LENGTH: 30
<212> TYPE: DNA
<213> ORGANISM: Artificial Sequence
<220> FEATURE:
<223> OTHER INFORMATION: synthetic primer

<400> SEQUENCE: 55
agcttggcat tgaaaactac gtattttggg                                  30

<210> SEQ ID NO 56
<211> LENGTH: 30
<212> TYPE: DNA
<213> ORGANISM: Artificial Sequence
<220> FEATURE:
<223> OTHER INFORMATION: synthetic primer

<400> SEQUENCE: 56
gtagttttca atgccaagct ccttagtaat                                  30

<210> SEQ ID NO 57
<211> LENGTH: 30
<212> TYPE: DNA
<213> ORGANISM: Artificial Sequence
<220> FEATURE:
<223> OTHER INFORMATION: synthetic primer

<400> SEQUENCE: 57
agcttggcac agaaaactac gtattttggg                                  30

<210> SEQ ID NO 58
<211> LENGTH: 30
<212> TYPE: DNA
<213> ORGANISM: Artificial Sequence
<220> FEATURE:
<223> OTHER INFORMATION: synthetic primer

<400> SEQUENCE: 58
gtagttttct gtgccaagct ccttagtaat                                  30

<210> SEQ ID NO 59
<211> LENGTH: 30
<212> TYPE: DNA
<213> ORGANISM: Artificial Sequence
<220> FEATURE:
<223> OTHER INFORMATION: synthetic primer

<400> SEQUENCE: 59
agcttggcgt ggaaaactac gtattttggg                                  30

<210> SEQ ID NO 60
<211> LENGTH: 30
<212> TYPE: DNA
<213> ORGANISM: Artificial Sequence
<220> FEATURE:
<223> OTHER INFORMATION: synthetic primer

<400> SEQUENCE: 60
```
gtagttttcc acgccaagct ccttagtaat         30

<210> SEQ ID NO 61
<211> LENGTH: 30
<212> TYPE: DNA
<213> ORGANISM: Artificial Sequence
<220> FEATURE:
<223> OTHER INFORMATION: synthetic primer

<400> SEQUENCE: 61
actacgtagg ctggggtgga agagaagggt         30

<210> SEQ ID NO 62
<211> LENGTH: 30
<212> TYPE: DNA
<213> ORGANISM: Artificial Sequence
<220> FEATURE:
<223> OTHER INFORMATION: synthetic primer

<400> SEQUENCE: 62
ccaccccagc ctacgtagtt ttcgcggcca         30

<210> SEQ ID NO 63
<211> LENGTH: 30
<212> TYPE: DNA
<213> ORGANISM: Artificial Sequence
<220> FEATURE:
<223> OTHER INFORMATION: synthetic primer

<400> SEQUENCE: 63
actacgtaag ctggggtgga agagaagggt         30

<210> SEQ ID NO 64
<211> LENGTH: 30
<212> TYPE: DNA
<213> ORGANISM: Artificial Sequence
<220> FEATURE:
<223> OTHER INFORMATION: synthetic primer

<400> SEQUENCE: 64
ccaccccagc ttacgtagtt ttcgcggcca         30

<210> SEQ ID NO 65
<211> LENGTH: 30
<212> TYPE: DNA
<213> ORGANISM: Artificial Sequence
<220> FEATURE:
<223> OTHER INFORMATION: synthetic primer

<400> SEQUENCE: 65
actacgtagc gtggggtgga agagaagggt         30

<210> SEQ ID NO 66
<211> LENGTH: 30
<212> TYPE: DNA
<213> ORGANISM: Artificial Sequence
<220> FEATURE:
<223> OTHER INFORMATION: synthetic primer

<400> SEQUENCE: 66
ccaccccacg ctacgtagtt ttcgcggcca         30

<210> SEQ ID NO 67
<211> LENGTH: 30
<212> TYPE: DNA
<213> ORGANISM: Artificial Sequence
<220> FEATURE:

```
<223> OTHER INFORMATION: synthetic primer

<400> SEQUENCE: 67
actacgtacc gtggggtgga agagaagggt                              30

<210> SEQ ID NO 68
<211> LENGTH: 30
<212> TYPE: DNA
<213> ORGANISM: Artificial Sequence
<220> FEATURE:
<223> OTHER INFORMATION: synthetic primer

<400> SEQUENCE: 68
ccaccccacg gtacgtagtt ttcgcggcca                              30

<210> SEQ ID NO 69
<211> LENGTH: 31
<212> TYPE: DNA
<213> ORGANISM: Artificial Sequence
<220> FEATURE:
<223> OTHER INFORMATION: synthetic primer

<400> SEQUENCE: 69
gacgcaaata ttggcgacat gcttttagga t                            31

<210> SEQ ID NO 70
<211> LENGTH: 31
<212> TYPE: DNA
<213> ORGANISM: Artificial Sequence
<220> FEATURE:
<223> OTHER INFORMATION: synthetic primer

<400> SEQUENCE: 70
catgtcgcca atatttgcgt cgattgatcc t                            31

<210> SEQ ID NO 71
<211> LENGTH: 31
<212> TYPE: DNA
<213> ORGANISM: Artificial Sequence
<220> FEATURE:
<223> OTHER INFORMATION: synthetic primer

<400> SEQUENCE: 71
gacgcaaatt atggcgacat gcttttagga t                            31

<210> SEQ ID NO 72
<211> LENGTH: 31
<212> TYPE: DNA
<213> ORGANISM: Artificial Sequence
<220> FEATURE:
<223> OTHER INFORMATION: synthetic primer

<400> SEQUENCE: 72
catgtcgcca taatttgcgt cgattgatcc t                            31

<210> SEQ ID NO 73
<211> LENGTH: 31
<212> TYPE: DNA
<213> ORGANISM: Artificial Sequence
<220> FEATURE:
<223> OTHER INFORMATION: synthetic primer

<400> SEQUENCE: 73
gacgcaaatt gcggcgacat gcttttagga t                            31

<210> SEQ ID NO 74
```

-continued

<211> LENGTH: 31
<212> TYPE: DNA
<213> ORGANISM: Artificial Sequence
<220> FEATURE:
<223> OTHER INFORMATION: synthetic primer

<400> SEQUENCE: 74
catgtcgccg caatttgcgt cgattgatcc t                                         31

<210> SEQ ID NO 75
<211> LENGTH: 31
<212> TYPE: DNA
<213> ORGANISM: Artificial Sequence
<220> FEATURE:
<223> OTHER INFORMATION: synthetic primer

<400> SEQUENCE: 75
gacgcaaata tgggcgacat gcttttagga t                                         31

<210> SEQ ID NO 76
<211> LENGTH: 31
<212> TYPE: DNA
<213> ORGANISM: Artificial Sequence
<220> FEATURE:
<223> OTHER INFORMATION: synthetic primer

<400> SEQUENCE: 76
catgtcgccc atatttgcgt cgattgatcc t                                         31

<210> SEQ ID NO 77
<211> LENGTH: 33
<212> TYPE: DNA
<213> ORGANISM: Artificial Sequence
<220> FEATURE:
<223> OTHER INFORMATION: synthetic primer

<400> SEQUENCE: 77
tgacgcaaat caaggcgaca tgctttggg atg                                        33

<210> SEQ ID NO 78
<211> LENGTH: 33
<212> TYPE: DNA
<213> ORGANISM: Artificial Sequence
<220> FEATURE:
<223> OTHER INFORMATION: synthetic primer

<400> SEQUENCE: 78
gcatgtcgcc ttgatttgcg tcgattgatc cta                                       33

<210> SEQ ID NO 79
<211> LENGTH: 31
<212> TYPE: DNA
<213> ORGANISM: Artificial Sequence
<220> FEATURE:
<223> OTHER INFORMATION: synthetic primer

<400> SEQUENCE: 79
gacgcaaatg aaggcgacat gcttttagga t                                         31

<210> SEQ ID NO 80
<211> LENGTH: 31
<212> TYPE: DNA
<213> ORGANISM: Artificial Sequence

```
<220> FEATURE:
<223> OTHER INFORMATION: synthetic primer

<400> SEQUENCE: 80
catgtcgcct tcatttgcgt cgattgatcc t                                  31
```

US 7,919,300 B2

GLUCOSE ISOMERASE MUTANTS

FIELD OF THE INVENTION

The present invention relates to molecular biology and biotechnology, and more specifically relates to recombinant glucose isomerases having improved activity or improved activity and thermostability, their preparation and uses thereof.

The Sequence Listing submitted in text format (.txt) herewith, named "sequence_ST25.txt, (created on Tuesday, Sep. 14, 2010, 126 KB), is incorporated herein by reference.

BACKGROUND OF THE INVENTION

Glucose isomerase (E.C.5.3.1.5) or xylose isomerase or D-xylose ketol isomerase is a key enzyme in the pentose phosphate pathway, catalyzing the conversion of D-xylose to D-xylulose. The isomerase also converts D-glucose to fructose and therefore is one of the most important enzymes in the food and beverage industry for the manufacture of fructose syrup (Kaneko et al., *Biosci Biotechnol Biochem.* 2000, 64: 940-947). The equilibrium of the isomerization of D-glucose to fructose is primarily dictated by the temperature of the reaction. The higher the temperature, the more the fructose in the final mixture of fructose and glucose. At present the commercial glucose isomerases come mainly from *Actinoplanes missouriensis*, *Bacillus coagulans*, *Streptomyces rubiginosus* and *Streptomyces murinus*, and are not stable at temperature above 65° C. Consequently, the current commercial isomerization is restricted to operate at around 60° C. and the products normally contain no more than 44% of fructose. The HFCS-55 (high fructose corn syrup containing 55% fructose) used in beverage and other industries is usually obtained by expensive chromatographic enrichment.

The scientists around the world have been working on the identification and protein engineering of thermostable and highly active glucose isomerases from thermophilic bacteria. J. G. Zeikus and his collaborators have isolated and studied thermostable glucose isomerases from thermophilic bacteria *Thermoanaerobacterium saccharolyticum* and *Thermotoga neapolitana* (Lee et al., *Journal of General Microbiology*, 139:1227-1234, 1993; Vieille et al., *Methods Enzymology*, 330:215-24, 2001; Lee et al., *Journal of General Microbiology*, 139:1241-1243, 1993; Scriprapundh et al., *Protein Engineering*, 13:259-265, 2000); Scriprapundh et al., *Protein Engineering*, 16:683-690, 2003; Zeikus et al., U.S. Pat. No. 5,656,497)). Nevertheless, the thermostability and the activity of these and other thermostable glucose isomerases have not yet met the requirements for industry applications. Thus, a glucose isomerases having improved activity or improved activity and thermostability is still desired for the industrial application.

DETAILED DESCRIPTION OF THE INVENTION

Present invention has shown our efforts of genetic and protein engineering of *Thermoanaerobacterium saccharolyticum* glucose isomerase to generate a series of glucose isomerases with improved catalytic activity and thermostability suitable for the production of fructose syrup containing high concentration of fructose.

The objective of present invention is to provide thermostable and highly active recombinant glucose isomerases. Another objective of the invention is to apply the obtained recombinant glucose isomerases to produce directly fructose syrup containing 55 wt % or higher concentration of fructose.

Still another objective of the invention is to apply the recombinant glucose isomerases to produce fructose syrup containing less than 55 wt % fructose.

The inventors of the present invention have introduced mutations, by site-directed mutagenesis, into a wild type of *T. saccharolyticum* glucose isomerase gene and obtained a series of highly active or highly active and thermostable glucose isomerase mutants after screening the candidate mutants on MacConkey agar plates. More specifically, the process of generating the mutants include: construction of plasmid carrying the wild-type *T. saccharolyticum* glucose isomerase gene; determination of the mutation sites and the mutations to be introduced; design of the primers used for the site-directed mutagenesis; PCR amplification of the DNA fragments with the wild-type glucose isomerase gene as the template; assembly and amplification of the DNA fragments into a full-length gene containing the mutations; cloning of the mutant gene into an appropriate vector; transformation of the vector containing the gene into an appropriate bacterial host; screening of the transformants for clones carrying desired glucose isomerase; isolation of the plasmid DNA from the positive clones; and determination of the DNA sequences of the glucose isomerase mutants.

For the preparation of the novel glucose isomerase mutants of present invention, any suitable vector can be employed. The suitable vectors include but not are limited to prokaryotic expression vectors such as pGEMT-Easy, pRSET-A and pET21; include but are not limited to eukaryotic expression vectors such as pYD1 and pYES2/GS; include but are not limited to cloning vectors such as pUC 18/19 and pBluescript®-SK(+/−).

For the preparation of the novel glucose isomerase mutants of present invention, any suitable host cell is applicable. The host cells can be either prokaryotic or eukaryotic cells. The suitable prokaryotic cells include but are not limited to *E. coli*, *Bacillus subtilis*, *Bacillus brevis*, *Bacillus megaterium* (e.g. *Bacillus megaterium* BP931), *T. saccharolyticum* and *Streptomyces* (e.g. *S. diastaticus* M1033). The suitable eukaryotic cells include but are not limited to *Saccharomyces cerevisiae* and *Pichia pastoris* (e.g. *P. pastori* GS115/9891).

For the preparation of the novel glucose isomerase mutants of present invention, the resulted gene encoding the mutants can be appropriately expressed. Through applying the knowledge well known to whose skilled in the field, a person skilled in the art can readily express the recombinant glucose isomerases as intra-cellular or extra-cellular proteins in prokaryotic or eukaryotic cells.

The present invention provides a glucose isomerase mutant comprising at least one mutation selected from a group consisting of position 139, position 182, position 187 and position 299 in reference to SEQ ID NO.: 2 in the Sequence Listing, and having at lease 50%-150% higher specific glucose isomerase activity of converting D-glucose to fructose than the wild-type glucose isomerase shown as SEQ ID NO.: 2 in the Sequence Listing, preferably 150-250% higher, and more preferably 250% higher. The preferred are those glucose isomerase mutants that, in reference to SEQ ID NO.: 2 in the Sequence Listing, comprise at least one mutation selected from a group consisting of change of tryptophan at position 139 to any other 19 natural amino acids, change of arginine at position 182 to any other 19 natural amino acids, change of phenylalanine at position 187 to any other 19 natural amino acids, and change of threonine at position 299 to any other 19 natural amino acids, and has at lease 50% higher specific glucose isomerase activity of converting D-glucose than the wild-type glucose isomerase shown as SEQ ID NO.: 2 in the Sequence Listing. The more preferred are those glucose isomerase mutants that, in reference to SEQ ID NO.: 2 in the Sequence Listing, comprise the mutation of tryptophan at position 139 to lysine, or serine, or cysteine, or isoleucine, or threonine, or asparagine, or phenylalanine; or/and arginine at position 182 to proline, or serine, or alanine, or isoleucine, or threonine, or valine; or/and phenylalanine at position 187 to glycine, or serine, or alanine, or proline; or/and threonine at position 299 to isoleucine, or tyrosine, or cysteine, or methionine, or glutamic acid, or glutamine. The most preferred are those glucose isomerase mutants listed in Table 2 below.

The mutants of the present invention have high catalytic activity towards D-glucose, and are thermostable and tolerant to low pH. For example, MGI-4, one of the mutants of present invention, is 651% more active than the wild-type glucose isomerase, maintains 50% or more of the activity after heat treatment of 16 hours at 80° C., and at pH 5.0 maintains approximately 80% of the activity under the optimal pH (pH 7.0). MGI-3, another of such mutants, is 412% more active than the wild-type glucose isomerase, maintains 50% or more of the activity after heat treatment of 21 hours at 80° C., and at pH 5.0 maintains approximately 70% of the activity under the optimal pH (pH 7.0).

The highly active and thermostable glucose isomerase mutants of the present invention can be used for directly production of fructose syrup containing 55 wt % or higher concentration of fructose, or used for the production of fructose syrup containing less than 55 wt % fructose. The recombinant isomerase mutants of the present invention can be used as un-purified, crude extract, or as partially purified enzyme, or as purified enzyme. In addition, for various industrial applications, the recombinant enzymes can be prepared as immobilized cell or immobilized enzymes by use of the knowledge well known to whose skilled in the field.

DEFINITIONS

The term "wild-type" or "wild type" used herein refers to the glucose isomerase of *Thermoanaerobacterium saccharolyticum* ATCC 49915 with its nucleotide sequence as shown in SEQ ID NO.: 1 and with its amino acid sequence as shown in SEQ ID NO.: 2 in the Sequence Listing. The DNA sequence of the wild-type glucose isomerase used in the present invention is different from that of the published DNA sequence of a glucose isomerase from the same species (Lee et al., *Journal of General Microbiology*, 139:1227-1234, 1993; GenBank L09699) in that the nucleotides at position 241-242 of the wild-type glucose isomerase are GC, encoding alanine (Ala) at the amino acid position 81; while the corresponding nucleotides of GenBank L09699 are CG, encoding arginine (Arg) at the amino acid position.

The term "reference sequence" used herein means SEQ ID NO.:1 in the Sequencing Listing when it refers to a DNA sequence; and means SEQ ID NO.: 2 in the Sequencing Listing when it refers to an amino acid sequence. The alignment of the reference sequence and the sequences of the glucose isomerase mutants of the present invention can be done manually or by computer (for example, using computer softwares CLUSTALW, AMAS, and DIALIGN).

The term "position" or "position x" used herein, where x is a numeral, in the present invention refers to the position of the nucleotide or amino acid of the mutant sequences that does not match to the reference sequence, SEQ ID NO.: 1 or SEQ ID NO.: 2 in the Sequence Listing, when the alignment between the mutant glucose isomerases of the present invention and the wild-type glucose isomerase reaches maximum in homology.

The term "glucose isomerase mutant(s)" used herein refers to an enzyme that, in comparison of the reference sequence SEQ ID NO.:2 in the Sequence Listing, comprises at least one amino acid mutation at a position selected from positions 139, 182, 187 and 299 and has glucose isomerase activity towards D-glucose at least 50% higher than the wild-type *T. saccharolyticum* glucose isomerase. The glucose isomerase mutants of the present invention include the mutants specifically displayed in SEQ ID NO.: 4 in the Sequencing Listing; their derivatives of having conservative substitutions, or adding one or more amino acids in or deleting one or more amino acids from SEQ ID NO.: 4. The mutants of the present invention also encomprise the derivatives of N-terminus truncation, C-terminus truncation, and partial or complete repetition of SEQ ID NO.: 4.

IUPAC nomenclature and symbolism for amino acid abbreviations (one-letter code or three-letter code) was used in the present invention (*Eur. J. Biochem.*, 138:9-37, 1984).

BRIEF DESCRIPTION OF THE DRAWINGS

FIG. 1 shows the polyacrylamide gel electrophoresis of glucose isomerase mutant MGI-4. The four lanes from left to right are protein molecular weight markers, crude glucose isomerase mutant MGI-4, BSA, and partially purified glucose isomerase mutant MGI-4 respectively. (Please refers to Example 10 for the preparation of crude and partially purified glucose isomerase mutant MGI-4).

FIG. 2 shows the efficient conversion of D-glucose to fructose by glucose isomerase mutant MGI-4 at 80 C. The black column represents the amount of remaining glucose and the grey column beneath, the amount of fructose formed. The figure indicates that the rate of fructose formation was in linear relation to the reaction time during the first two hours and the rate decreased afterwards.

FIG. 3 shows the thermal stability of the wild-type glucose isomerase and glucose isomerase mutants at 80° C. Wildtype, the wild-type glucose isomerase; MGI-2, MGI-3 and MGI-4, the glucose isomerase mutants containing two, three or four mutations as described in detail in Examples 6-8.

FIG. 4 shows the effect of pH to the wild-type glucose isomerase and glucose isomerase mutants. Wild-type, the wild-type glucose isomerase; MGI-2, MGI-3 and MGI-4, the glucose isomerase mutants containing two, three or four mutations as described in detail in Examples 6-8.

EXAMPLES

The examples described below are for illustration of the invention only and are not intended to be regarded as the limitation of the invention. In the following examples, conventional practice or manufactures' suggestion/protocol was followed in the cases where the conditions were not specified.

Example 1

Amplification of Wild-Type Glucose Isomerase and Construction of pGEMT-TS

Primers T1 and T2 (see Table 1 below) were designed based on the sequence of GenBank L09699 and used to amplify the wild-type glucose isomerase gene from *T. saccharolyticum* ATCC 49915 (from ATCC, USA). The amplification condition was: 20 mM Tris-HCl (pH 8.8), 10 mM KCl, 10 mM $(NH_4)_2SO_4$, 2 mM $MgSO_4$, 0.1% Triton X-100, 0.4 µM Primer T1, 0.4 µM Primer T2, 50 µM dATP, 50 µM dTTP, 50 µM dCTP, 50 µM dGTP, 1.5 U Taq DNA polymerase (Promega, USA), a loopful of *T. saccharolyticum* colony, and the total volume was adjusted to 50 µl with distilled water. The PCR amplification program for the reaction was: 95° C., 3 min; then 40 cycles of 95° C., 50 seconds, 50° C., 30 seconds, 72° C., 60 seconds; and with an additional 10 minutes at 72° C. at the end of the reaction. The amplified PCR product, about 1.5 kb in length, was ligated with pGEMT-Easy to generate pGEMT-TS. PGEMT-TS was sequenced to determine the DNA sequence of the cloned wild-type glucose isomerase as SEQ ID NO.: 1 in the Sequence Listing and the corresponding amino acid sequence as SEQ ID NO.: 2 in the Sequence Listing. The DNA sequence of the wild-type glucose isomerase is different from that of the published DNA sequence of a glucose isomerase from the same species (Lee et al., *Journal of General Microbiology*, 139:1227-1234, 1993; GenBank L09699) in that the nucleotides of our wide-type glucose isomerase at position 241-242 are GC encoding alanine (Ala) at the amino acid position 81; while the corresponding nucleotides of GenBank L09699 are CG encoding arginine (Arg) at the same amino acid position.

Example 2

Site-Directed Mutagenesis of Trp 139 of Wild-Type Glucose Isomerase

The site directed mutagenesis was carried out as described by Ho et al. (Gene 77:51-59, 1989) and White et al. (PCR Protocols: current methods and applications. Totowa, N.J.: Humana Press, 1993), with modifications.

Using pGEMT-TS (see Example 1) as the template, Primers 139FF and 139FR (see Table 1 below) were synthesized to mutate the Trp (W) at the position 139 of the wild-type glucose isomerase to Phe (F) to generate glucose isomerase mutant MGI-W139F. Fragment T1FR was amplified using primer pair T1 (see Table 1 below) and 139FR. Fragment FFT2 was amplified using primer pair 139FF and T2 (see Table 1 below). The amplification condition was: 20 mM Tris-HCl (pH 8.8), 10 mM KCl, 10 mM $(NH_4)_2SO_4$, 2 mM $MgSO_4$, 0.1% Triton X-100, 0.4 µM Primer T1 and 0.4 µM Primer 139FR (for fragment T1FR) or 0.4 µM Primer T2 and 0.4 µM Primer 139FF (for fragment FFT2), 50 µM dATP, 50 µM dTTP, 50 µM dCTP, 50 µM dGTP, 1.5 U Pfu DNA polymerase (Promega, USA), 20 ng pGEMT-TS, and the total volume was adjusted to 50 µl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The PCR products, fragment T1FR and fragment FFT2, were separated on 1% agarose gel and recovered using QIAquick Gel Extraction Kit (QIAGEN, German). The full-length glucose isomerase gene was then amplified on the following condition: 20 mM Tris-HCl (pH 8.8), 10 mM KCl, 10 mM $(NH_4)_2SO_4$, 2 mM $MgSO_4$, 0.1% Triton X-100, 0.4 µM Primer T1 and 0.4 µM Primer T2, 50 µM dATP, 50 µM dTTP, 50 µM dCTP, 50 µM dGTP, 1.5 U Pfu DNA polymerase, 20 ng fragment T1FR and 20 ng fragment FFT2, and the total volume was adjusted to 50 µl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The full-length mutant MGI-W139F was separated on 1% agarose gel and recovered using QIAquick Gel Extraction Kit (QIAGEN, German). Plasmid pGEMT-MGI-W139F, generated after ligation between MGI-W139F and pGEMT-Easy, was transformed into competent *E. coli* HB101 and the transformants were screened for clones of glucose isomerase activity on 1% MacConkey agar plates containing 1% D-xylose and 50 mg/L ampicillin. pGEMT-MGI-W139F DNA was then isolated from the positive clones and sequenced. The sequencing results confirmed that the desired site-mutation was correctly introduced. Its amino acid sequence was shown as SEQ ID NO.: 5 (see the Sequence Listing below).

Similarly, glucose isomerase mutants MGI-W139K, MGI-W139S, MGI-W139C, MGI-W139I, MGI-W139T and MGI-W139N were generated following the above procedures. The relevant primers are listed in Table 1 below. The amino acid sequences of these mutants are listed as SEQ ID NOs.: 6-11 in the Sequence Listing.

Example 3

Site-Directed Mutagenesis of Arg182 of Wild-Type Glucose Isomerase

The site directed mutagenesis was carried out as described by Ho et al. (Gene 77:51-59, 1989) and White et al. (PCR Protocols: current methods and applications. Totowa, N.J.: Humana Press, 1993), with modifications.

Using pGEMT-TS (see Example 1) as the template, Primers 182AF and 182AR (see Table 1) were synthesized to mutate the Arg (R) at the position 182 of the wild-type glucose isomerase to Ala (A) to generate glucose isomerase mutant MGI-R182A. Fragment T1AR was amplified using primer pair T1 (see Table 1) and 182AR. Fragment AFT2 was amplified using primer pair 182AF and T2 (see Table 1). The amplification condition was: 20 mM Tris-HCl (pH 8.8), 10 mM KCl, 10 mM $(NH_4)_2SO_4$, 2 mM $MgSO_4$, 0.1% Triton X-100, 0.4 µM Primer T1 and 0.4 µM Primer 182AR (for fragment T1AR) or 0.4 µM Primer T2 and 0.4 µM Primer 182AF (for fragment AFT2), 50 µM dATP, 50 µM dTTP, 50 µM dCTP, 50 µM dGTP, 1.5 U Pfu DNA polymerase, 20 ng pGEMT-TS, and the total volume was adjusted to 50 µl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The PCR products, fragment T1AR and fragment AFT2, were separated on 1% agarose gel and recovered using QIAquick Gel Extraction Kit (QIAGEN, German). The full-length glucose isomerase gene was then amplified on the following condition: 20 mM Tris-HCl (pH 8.8), 10 mM KCl, 10 mM $(NH_4)_2SO_4$, 2 mM $MgSO_4$, 0.1% TritonX-100, 0.4 µM Primer T1 and 0.4 µM Primer T2, 50 µM dATP, 50 µM dTTP, 50 µM dCTP, 50 µM dGTP, 1.5 U Pfu DNA polymerase, 20 ng fragment T1AR and 20 ng fragment AFT2, and the total volume was adjusted to 50 µl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The full-length mutant MGI-R182A was separated on 1% agarose gel and recovered using QIAquick Gel Extraction Kit (QIAGEN, German). Plasmid pGEMT-MGI-R182A, generated after ligation between MGI-R182A and pGEMT-Easy, was transformed into competent *E. coli* HB101 and the transformants were screened for clones of glucose isomerase activity on 1% MacConkey agar plates containing 1% D-xylose and 50 mg/L ampicillin. pGEMT-MGI-R182A DNA was then isolated from the positive clones and sequenced. The sequencing results confirmed that the desired site-mutation was correctly introduced. Its amino acid sequence was shown as SEQ ID NO.: 12 (see the Sequence Listing below).

Similarly, glucose isomerase mutants MGI-R182P, MGI-R182S, MGI-R182I, MGI-R182T and MGI-R182V were generated following the above procedures. The relevant primers are listed in Table 1 below. The amino acid sequences of these mutants are listed as SEQ ID NOS.: 13-17 in the Sequence Listing.

Example 4

Site-Directed Mutagenesis of Phe187 of Wild-Type Glucose Isomerase

The site directed mutagenesis was carried out as described by Ho et al. (Gene 77:51-59, 1989) and White et al. (PCR Protocols: current methods and applications. Totowa, N.J.: Humana Press, 1993), with modifications.

Using pGEMT-TS (see Example 1) as the template, Primers 187SF and 187SR (see Table 1) were synthesized to mutate the Phe (F) at the position 187 of the wild-type glucose isomerase to Ser (S) to generate glucose isomerase mutant MGI-F187S. Fragment T1SR was amplified using primer pair T1 (see Table 1) and 187SR. Fragment SFT2 was amplified using primer pair 187SF and T2 (see Table 1). The amplification condition was: 20 mM Tris-HCl (pH 8.8), 10 mM KCl, 10 mM MH$_4$)$_2$SO$_4$, 2 mM MgSO$_4$, 0.1% Triton X-100, 0.4 µM Primer T1 and 0.4 µM Primer 187SR (for fragment T1SR) or 0.4 µM Primer T2 and 0.4 µM Primer 187SF (for fragment SFT2), 50 µM dATP, 50 µM dTTP, 50 µM dCTP, 50 µM dGTP, 1.5 U Pfu DNA polymerase, 20 ng pGEMT-TS, and the total volume was adjusted to 50 µl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The PCR products, fragment T1SR and fragment SFT2, were separated on 1% agarose gel and recovered using QIAquick Gel Extraction Kit (QIAGEN, German). The full-length glucose isomerase gene was then amplified on the following condition: 20 mM Tris-HCl (pH 8.8), 10 mM KCl, 10 mM (NH$_4$)$_2$SO$_4$, 2 mM MgSO$_4$, 0.1% Triton X-100, 0.4 µM Primer T1 and 0.4 µM Primer T2, 50 µM dATP, 50 µM dTTP, 50 µM dCTP, 50 µM dGTP, 1.5 U Pfu DNA polymerase, 20 ng fragment T1SR and 20 ng fragment SFT2, and the total volume was adjusted to 50 µl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The full-length mutant MGI-F187S was separated on 1% agarose gel and recovered using QIAquick Gel Extraction Kit (QIAGEN, German). Plasmid pGEMT-MGI-F187S, generated after ligation between MGI-F187S and pGEMT-Easy, was transformed into competent E. coli HB 101 and the transformants were screened for clones of glucose isomerase activity on 1% MacConkey agar plates containing 1% D-xylose and 50 mg/L ampicillin. pGEMT-MGI-F187S DNA was then isolated from the positive clones and sequenced. The sequencing results confirmed that the desired site-mutation was correctly introduced. Its amino acid sequence was shown as SEQ ID NO.: 18 (see the Sequence Listing below).

Similarly, glucose isomerase mutants MGI-F187G, MGI-F187P and MGI-F187A were generated following the above procedures. The relevant primers are listed in Table 1. The amino acid sequences of these mutants are listed as SEQ ID Nos. 19-21 in Sequence Listing.

Example 5

Site-Directed Mutagenesis of Thr299 of Wild-Type Glucose Isomerase

The site directed mutagenesis was carried out as described by Ho et al. (Gene 77:51-59, 1989) and White et al. (PCR Protocols: current methods and applications. Totowa, N.J.: Humana Press, 1993), with modifications.

Using pGEMT-TS (see Example 1) as the template, Primers 299QF and 299QR (see Table 1) were synthesized to mutate the Thr (T) at the position 299 of the wild-type glucose isomerase to Gln (Q) to generate glucose isomerase mutant MGI-T299Q. Fragment T1QR was amplified using primer pair T1 (see Table 1) and 299QR. Fragment QFT2 was amplified using primer pair 299QF and T2 (see Table 1). The amplification condition was: 20 mM Tris-HCl (pH 8.8), 10 mM KCl, 10 mM (NH$_4$)$_2$SO$_4$, 2 mM MgSO$_4$, 0.1% Triton X-100, 0.4 µM Primer T1 and 0.4 µM Primer 299QR (for fragment T1QR) or 0.4 µM Primer T2 and 0.4 µM Primer 299QF (for fragment QFT2), 50 µM dATP, 50 µM dTTP, 50 µM dCTP, 50 µM dGTP, 1.5 U Pfu DNA polymerase, 20 ng pGEMT-TS, and the total volume was adjusted to 50 µl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The PCR products, fragment T1QR and fragment QFT2, were separated on 1% agarose gel and recovered using QIAquick Gel Extraction Kit (QIAGEN, German). The full-length glucose isomerase gene was then amplified on the following condition: 20 mM Tris-HCl (pH 8.8), 10 mM KCl, 10 mM (NH$_4$)$_2$SO$_4$, 2 mM MgSO$_4$, 0.1% Triton X-100, 0.4 µM Primer T1 and 0.4 µM Primer T2, 50 µM dATP, 50 µM dTTP, 50 µM dCTP, 50 µM dGTP, 1.5 U Pfu DNA polymerase, 20 ng fragment T1QR and 20 ng fragment QFT2, and the total volume was adjusted to 50 µl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The full-length mutant MGI-T299Q was separated on 1% agarose gel and recovered using QIAquick Gel Extraction Kit (QIAGEN, German). Plasmid pGEMT-MGI-T299Q, generated after ligation between MGI-T299Q and pGEMT-Easy, was transformed into competent E. coli HB101 and the transformants were screened for clones of glucose isomerase activity on 1% MacConkey agar plates containing 1% D-xylose and 50 mg/L ampicillin. pGEMT-MGI-T299Q DNA was then isolated from the positive clones and sequenced. The sequencing results confirmed that the desired site-mutation was correctly introduced. Its amino acid sequence was shown as SEQ ID NO.: 22 (see the Sequence Listing).

Similarly, glucose isomerase mutants MGI-T299I, MGI-T299Y, MGI-T299C, MGI-T299M and MGI-T299E were generated following the above procedures. The relevant primers are listed in Table 1. The amino acid sequences of these mutants are listed as SEQ ID NOS.: 23-27 in the Sequence Listing below.

Example 6

Generation of Glucose Isomerase Mutants MGI-2, MGI-2AQ and MGI-2FQ

The site directed mutagenesis was carried out as described by Ho et al. (Gene 77:51-59, 1989) and White et al. (PCR Protocols: current methods and applications. Totowa, N.J.: Humana Press, 1993), with modifications.

Fragment FFAR was amplified using primer pair 139FF (see Table 1) and 182AR (see Table 1) on the following condition: 20 mM Tris-HCl (pH 8.8), 10 mM KCl, 10 mM $(NH_4)_2SO_4$, 2 mM $MgSO_4$, 0.1% Triton X-100, 0.4 μM Primer 139FF and 0.4 μM Primer 182AR, 50 μM dATP, 50 μM dTTP, 50 μM dCTP, 50 μM dGTP, 1.5 U Pfu DNA polymerase, 20 ng pGEMT-TS, and the total volume was adjusted to 50 μl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The PCR product, fragment FFAR, was separated on 1% agarose gel and recovered using QIAquick Gel Extraction Kit (QIAGEN, German). The full-length glucose isomerase gene was then amplified on the following condition: 20 mM Tris-HCl (pH 8.8), 10 mM KCl, 10 mM $(NH_4)_2SO_4$, 2 mM $MgSO_4$, 0.1% Triton X-100, 0.4 μM Primer T1 and 0.4 μM Primer T2, 50 μM dATP, 50 μM dTTP, 50 μM dCTP, 50 μM dGTP, 1.5 U Pfu DNA polymerase, 20 ng fragment T1FR (see Example 2), 20 ng fragment AFT2 (see Example 3) and 20 ng fragment FFAR and the total volume was adjusted to 50 μl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The full-length mutant MGI-2 was separated on 1% agarose gel and recovered using QIAquick Gel Extraction Kit (QIAGEN, German). Plasmid pGEMT-MGI-2, generated after ligation between MGI-2 and pGEMT-Easy, was transformed into competent *E. coli* HB101 and the transformants were screened for clones of glucose isomerase activity on 1% MacConkey agar plates containing 1% D-xylose and 50 mg/L ampicillin. pGEMT-MGI-2 DNA was then isolated from the positive clones and sequenced. The sequencing results confirmed that the desired site-directed mutations were correctly introduced. Its amino acid sequence was shown as SEQ ID NO.: 28 (see the Sequence Listing).

Similarly, glucose isomerase mutants MGI-2AQ and MGI-2FQ were generated following the above procedures. Primer pairs of T1 and 182AR, 182A F and 299QR, 299QF and T2 (see Table 1) were used for the generation of MGI-2AQ, which contains the double mutation of R182A and T299Q. Primer pairs of T1 and 139AR, 139AF and 299QR, 299QF and T2 (see Table 1) were used for the generation of MGI-2FQ, which contains the double mutation of W139F and T299Q. The amino acid sequences of the two mutants are listed as SEQ ID NOS.: 29-30 in the Sequence Listing below.

Example 7

Generation of Glucose Isomerase Mutants MGI-3

The site directed mutagenesis was carried out as described by Ho et al. (Gene 77:51-59, 1989) and White et al. (PCR Protocols: current methods and applications. Totowa, N.J.: Humana Press, 1993), with modifications.

Fragment AFQR was amplified using primer pair 182AF (see Table 1) and 299QR (see Table 1) on the following condition: 20 mM Tris-HCl (pH 8.8), 10 mM KCl, 10 mM $(NH_4)_2SO_4$, 2 mM $MgSO_4$, 0.1% Triton X-100, 0.4 μM Primer 182AF and 0.4 μM Primer 299QR, 50 μM dATP, 50 μM dTTP, 50 μM dCTP, 50 μM dGTP, 1.5 U Pfu DNA polymerase, 20 ng pGEMT-TS, and the total volume was adjusted to 50 μl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The PCR product, fragment AFQR, was separated on 1% agarose gel and recovered using QIAquick Gel Extraction Kit (QIAGEN, German). The full-length glucose isomerase gene was then amplified on the following condition: 20 mM Tris-HCl (pH 8.8), 10 mM KCl, 10 mM $(NH_4)_2SO_4$, 2 mM $MgSO_4$, 0.1% Triton X-100, 0.4 μM Primer T1 and 0.4 μM Primer T2, 50 μM dATP, 50 μM dTTP, 50 μM dCTP, 50 μM dGTP, 1.5 U Pfu DNA polymerase, 20 ng fragment T1FR (Example 2), 20 ng fragment QFT2 (Example 5), 20 ng fragment FFAR (Example 6) and 20 ng fragment AFQR, and the total volume was adjusted to 50 μl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The full-length mutant MGI-3 was separated on 1% agarose gel and recovered using QIAquick Gel Extraction Kit (QIAGEN, German). Plasmid pGEMT-MGI-3, generated after ligation between MGI-3, which contains triple mutation of W139F, R182A and T299Q, and pGEMT-MGI-3 was transformed into competent *E. coli* HB 101 and the transformants were screened for clones of glucose isomerase activity on 1% MacConkey agar plates containing 1% D-xylose and 50 mg/L ampicillin. pGEMT-MGI-3 DNA was then isolated from the positive clones and sequenced. The sequencing results confirmed that the desired site-mutation was correctly introduced. Its amino acid sequence was shown as SEQ ID NO.: 31 (see the Sequence Listing below).

Example 8

Generation of Glucose Isomerase Mutants MGI-4

The site directed mutagenesis was carried out as described by Ho et al. (Gene 77:51-59, 1989) and White et al. (PCR Protocols: current methods and applications. Totowa, N.J.: Humana Press, 1993), with modifications.

Fragment AFSR was amplified using primer pair 182AF (see Table 1 below) and 187SR (see Table 1) on the following condition: 20 mM Tris-HCl (pH 8.8), 10 mM KCl, 10 mM $(NH_4)_2SO_4$, 2 mM $MgSO_4$, 0.1% Triton X-100, 0.4 μM Primer 182AF and 0.4 μM Primer 187SR, 50 μM DATP, 50 μM dTTP, 50 μM dCTP, 50 μM dGTP, 1.5 U Pfu DNA polymerase, 20 ng pGEMT-TS, and the total volume was adjusted to 50 μl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The PCR product, fragment AFSR, was separated on 1% agarose gel and recovered using QIAquick Gel Extraction Kit (QIAGEN, German). Fragment SFQR was amplified using primer pair 187SF (Example 4) and 299QR (Example 5) on the following condition: 20 mM Tris-HCl (pH 8.8), 10 mM KCl, 10 mM $(NH_4)_2SO_4$, 2 mM $MgSO_4$, 0.1% Triton X-100, 0.4 μM Primer 187SF and 0.4 μM Primer 299QR, 50 μM dATP, 50 μM dTTP, 50 μM dCTP, 50 μM dGTP, 1.5 U Pfu DNA polymerase, 20 ng pGEMT-TS, and the total volume was adjusted to 50 μl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The PCR product, fragment SFQR, was separated on 1% agarose gel and recovered using QIAquick Gel Extraction Kit (QIAGEN, German). The full-length glucose isomerase gene was then amplified on the following condition: 20 mM Tris-HCl (pH 8.8), 10 mM KCl, 10 mM (NH$_4$)$_2$SO$_4$, 2 mM MgSO$_4$, 0.1% Triton X-100, 0.4 μM Primer T1 and 0.4 μM Primer T2, 50 μM dATP, 50 μM dTTP, 50 μM dCTP, 50 μM dGTP, 1.5 U Pfu DNA polymerase, 20 ng fragment T1FR (Example 2), 20 ng fragment FFAR (Example 6), 20 ng fragment AFQR, 20 ng fragment SFQR and 20 ng fragment QFT2 (Example 5), and the total volume was adjusted to 50 μl with distilled water. The PCR amplification program for the reaction was: 95° C., 3 min; then 35 cycles of 95° C., 50 seconds, 52° C., 30 seconds, 72° C., 180 seconds; and with an additional 5 minutes at 72° C. at the end of the reaction. The full-length mutant MGI-4 was separated on 1% agarose gel and recovered using QIAquick Gel Extraction Kit (QIAGEN, German). Plasmid pGEMT-MGI-4, generated after ligation between MGI-4 and pGEMT-Easy, was transformed into competent E. coli HB101 and the transformants were screened for clones of glucose isomerase activity on 1% MacConkey agar plates containing 1% D-xylose and 50 mg/L ampicillin. pGEMT-MGI-4 DNA was then isolated from the positive clones and sequenced. The sequencing results confirmed that the desired site-directed mutations were correctly introduced. Its amino acid sequence was shown as SEQ ID NO.: 32 (see the Sequence Listing below).

The primers used for the amplification of wild-type glucose isomerase and mutants described in Examples 1-8 are listed in Table 1 below.

TABLE 1

The Primers Used For Amplification of Wild-type Glucose Isomerase (wild-type) and the Mutants

| Products | Primers |
|---|---|
| Wild-type | T1:(SEQ ID NO: 33):<br>5' AGCCTAGGTTAATTAACTTTAAGAAGGAGATATACAT ATGAATAAATATTTTGAGA 3'<br>T2:(SEQ ID NO: 34):<br>5' ATAAGCTCAGCGGCGCGCCTTATTCTGCAAACAAATA C 3' |
| Mutant MGI-W139K | 139KF:(SEQ ID NO: 35):<br>5' AAGTTTTGAAAGGTACCGCAAATCTTTTCT 3'<br>139KR:(SEQ ID NO: 36):<br>5' TGCGGTACCTTTCAAAACTTTTGTCTTGCT 3' |
| Mutant MGI-W139S | 139SF:(SEQ ID NO: 37):<br>5' AAGTTTTGTCAGGTACCGCAAATCTTTTCT 3'<br>139SR:(SEQ ID NO: 38):<br>5' TGCGGTACCTGACAAAACTTTTGTCTTGCT 3' |
| Mutant MGI-W139C | 139CF:(SEQ ID NO: 39):<br>5' AAGTTTTGTGCGGTACCGCAAATCTTTTCT 3'<br>139CR:(SEQ ID NO: 40):<br>5' TGCGGTACCGCACAAAACTTTTGTCTTGCT 3' |
| Mutant MGI-W139I | 139IF:(SEQ ID NO: 41):<br>5' AAGTTTTGATTGGTACCGCAAATCTTTTCT 3'<br>139IR:(SEQ ID NO: 42):<br>5' TGCGGTACCAATCAAAACTTTTGTCTTGCT 3' |
| Mutant MGI-W139T | 139TF:(SEQ ID NO: 43):<br>5' AAGTTTTGACAGGTACCGCAAATCTTTTCT 3'<br>139TR:(SEQ ID NO: 44):<br>5' TGCGGTACCTGTCAAAACTTTTGTCTTGCT 3 |
| Mutant MGI-W139N | 139NF:(SEQ ID NO: 45):<br>5' AAGTTTTGAACGGTACCGCAAATCTTTTCT 3'<br>139NR:(SEQ ID NO: 46):<br>5' TGCGGTACCGTTCAAAACTTTTGTCTTGCT 3' |
| Mutant MGI-W139F | 139FF:(SEQ ID NO: 47):<br>5' AAAAGTTTTGTTTGGTACCGCAAATCTTTTCTC 3'<br>139FR:(SEQ ID NO: 48):<br>5' TTGCGGTACCAAACAAAACTTTTGTCTTGCTGG 3' |

TABLE 1-continued

The Primers Used For Amplification of Wild-type Glucose Isomerase (wild-type) and the Mutants

| Products | Primers |
|---|---|
| Mutant MGI-R182P | A182PF:(SEQ ID NO: 49):<br>5' AGCTTGGCCCGGAAAACTACGTATTTTGGG 3'<br>A182PR:(SEQ ID NO: 50):<br>5' GTAGTTTTCCGGGCCAAGCTCCTTAGTAAT 3' |
| Mutant MGI-R182S | 182SF:(SEQ ID NO: 51):<br>5' AGCTTGGCTCAGAAAACTACGTATTTTGGG 3'<br>182SR:(SEQ ID NO: 52):<br>5' GTAGTTTTCTGAGCCAAGCTCCTTAGTAAT 3' |
| Mutant MGI-R182A | 182AF:(SEQ ID NO: 53):<br>5' GGAGCTTGGCGCGGAAAACTACGTATTTTGGGG 3'<br>182AR:(SEQ ID NO: 54):<br>5' CGTAGTTTTCCGCGCCAAGCTCCTTAGTAATCT 3' |
| Mutant MGI-R182I | 182IF:(SEQ ID NO: 55):<br>5' AGCTTGGCATTGAAAACTACGTATTTTGGG 3'<br>182IR:(SEQ ID NO: 56):<br>5' GTAGTTTTCAATGCCAAGCTCCTTAGTAAT 3' |
| Mutant MGI-R182T | 182TF:(SEQ ID NO: 57):<br>5' AGCTTGGCACAGAAAACTACGTATTTTGGG 3'<br>182TR:(SEQ ID NO: 58):<br>5' GTAGTTTTCTGTGCCAAGCTCCTTAGTAAT 3' |
| Mutant MGI-R182V | 182VF:(SEQ ID NO: 59):<br>5' AGCTTGGCGTGGAAAACTACGTATTTTGGG 3'<br>182VR:(SEQ ID NO: 60):<br>5' GTAGTTTTCCACGCCAAGCTCCTTAGTAAT 3' |
| Mutant MGI-F187G | 187GF:(SEQ ID NO: 61):<br>5' ACTACGTAGGCTGGGGTGGAAGAGAAGGGT 3'<br>187GR:(SEQ ID NO: 62):<br>5' CCACCCCAGCCTACGTAGTTTTCGCGGCCA 3' |
| Mutant MGI-F187S | 187SF:(SEQ ID NO: 63):<br>5' ACTACGTAAGCTGGGGTGGAAGAGAAGGGT 3'<br>187SR:(SEQ ID NO: 64):<br>5' CCACCCCAGCTTACGTAGTTTTCGCGGCCA 3' |
| Mutant MGI-F187A | 187AF:(SEQ ID NO: 65):<br>5' ACTACGTAGCGTGGGGTGGAAGAGAAGGGT 3'<br>187AR:(SEQ ID NO: 66):<br>5' CCACCCCACGCTACGTAGTTTTCGCGGCCA 3' |
| Mutant MGI-F187P | 187PF:(SEQ ID NO: 67):<br>5' ACTACGTACCGTGGGGTGGAAGAGAAGGGT 3'<br>187PR:(SEQ ID NO: 68):<br>5' CCACCCCACGGTACGTAGTTTTCGCGGCCA 3' |
| Mutant MGI-T299I | 299IF:(SEQ ID NO: 69):<br>5' GACGCAAATATTGGCGACATGCTTTTAGGAT 3'<br>299IR:(SEQ ID NO: 70):<br>5' CATGTCGCCAATATTTGCGTCGATTGATCCT 3' |
| Mutant MGI-T299Y | 299YF:(SEQ ID NO: 71):<br>5' GACGCAAATTATGGCGACATGCTTTTAGGAT 3'<br>299YR:(SEQ ID NO: 72):<br>5' CATGTCGCCATAATTTGCGTCGATTGATCCT 3' |
| Mutant MGI-T299C | 299CF:(SEQ ID NO: 73):<br>5' GACGCAAATTGCGGCGACATGCTTTTAGGAT 3'<br>299CR:(SEQ ID NO: 74):<br>5' CATGTCGCCGCAATTTGCGTCGATTGATCCT 3' |
| Mutant MGI-T299M | 299MF:(SEQ ID NO: 75):<br>5' GACGCAAATATGGGCGACATGCTTTTAGGAT 3'<br>299MR:(SEQ ID NO: 76):<br>5' CATGTCGCCCATATTTGCGTCGATTGATCCT 3' |
| Mutant MGI-T299Q | 299QF:(SEQ ID NO: 77):<br>5' TGACGCAAATCAAGGCGACATGCTTTGGGATG 3'<br>299QR:(SEQ ID NO: 78):<br>5' GCATGTCGCCTTGATTTGCGTCGATTGATCCTA 3' |

TABLE 1-continued

The Primers Used For Amplification of Wild-type
Glucose Isomerase (wild-type) and the Mutants

| Products | Primers |
|---|---|
| Mutant MGI-T299E | 299EF:(SEQ ID NO: 79):<br>5' GACGCAAATGAAGGCGACATGCTTTTAGGAT 3'<br>299ER:(SEQ ID NO: 80):<br>5' CATGTCGCCTTCATTTGCGTCGATTGATCCT 3' |

Example 9

Isolation and Purification of Wild-Type Glucose Isomerase

The isolation and purification of wild-type glucose isomerase were based on Lee et al., (*Journal of General Microbiology*, 139:1227-1234, 1993) with modifications. pGEMT-TS transformed *E. coli* HB101 cells were incubated on 1% MacConkey agar plate containing 1% xylose and 50 mg/L ampicillin at 37° C. for 36 hours. A single colony from the plate was inoculated and cultivated in 5 mL LB supplemented with 50 mg/L ampicillin for 16 hours. The bacterial cells were pelleted and resuspended in 1 ml 20 mM phosphate buffer (pH 6.5), and $CoCl_2$ and $MgCl_2$ were added to final concentration of 250 µM and 5 mM, respectively. The cells were disrupted by using ultrasonication and centrifuged at 17,800 g for 15 minutes at 10° C. to collect the supernatant as crude glucose isomerase. The crude enzyme was heated at 80° C. for 10 minutes and centrifuged again at 17,800 g for 15 minutes at 10° C. to remove the precipitation. The resultant partially purified glucose isomerase was used in the subsequent assays and for the conversion of D-glucose to fructose as described below and shown in FIG. 2.

Example 10

Isolation and Purification of Glucose Isomerase Mutants

The isolation and purification of glucose isomerase mutant MGI-4 were as described in Example 9, except the plasmid used was pGEMT-MGI-4. The partially purified enzyme was shown on FIG. 1. Other glucose isomerase mutants were also isolated and purified as described in Example 9.

Example 11

Activity Assay of Wild-Type Glucose Isomerase with D-glucose as the Substrate

Substrate solution A stock containing 1.0 M D-glucose, 20 mM sodium phosphate buffer (pH 6.5), 250 µM $CoCl_2$ (final concentration) and 5 mM $MgCl_2$ (final concentration) was adjusted to pH 6.5. Ninety µl of the stock solution was mixed with 10 µl of the glucose isomerase prepared as described in Example 9, incubated at 80° C. for 10 minutes and quenched on ice immediately. The fructose formed was measured by the cysteine-carbazole method (Dische et al., *J. Biol. Chem,* 192: 583-587, 1951; and Nakamura, *Agr. Biol. Chem.* 32:701-706, 1968). The protein concentration was determined using Coomassie® Plus Protein Assay Reagent Kit (Pierce, USA) and SDD-PAGE, with BSA as the standard. One unit of enzyme activity was defined as the amount of enzyme needed for producing 1 µmole of fructose from D-glucose per minute under the assay condition. Table 2 below shows the specific activity of wild-type glucose isomerase.

Example 12

Activity Assay of Glucose Isomerase Mutants with D-glucose as the Substrate

The activity of glucose isomerase mutant MGI-4 was measured as described in Example 11. The activities of other glucose isomerase mutants were also measured as described in Example 11. Table 2 below shows the comparison of the specific activities of wild-type glucose isomerase and the mutants.

TABLE 2

The Activities of Wild-type Glucose Isomerase and the Mutants

| Enzyme | Amino Acid Sequence | Specific Activity |
|---|---|---|
| Wild-type | SEQ ID NO.: 2 | 100 |
| MGI-W139S | SEQ ID NO.: 7 | 392 |
| MGI-W139K | SEQ ID NO.: 6 | 246 |
| MGI-W139C | SEQ ID NO.: 8 | 382 |
| MGI-W139I | SEQ ID NO.: 9 | 329 |
| MGI-W139T | SEQ ID NO.: 10 | 254 |
| MGI-W139N | SEQ ID NO.: 11 | 376 |
| MGI-W139F | SEQ ID NO.: 5 | 195 |
| MGI-R182P | SEQ ID NO.: 13 | 264 |
| MGI-R182S | SEQ ID NO.: 14 | 327 |
| MGI-R182A | SEQ ID NO.: 12 | 195 |
| MGI-R182I | SEQ ID NO.: 15 | 654 |
| MGI-R182T | SEQ ID NO.: 16 | 287 |
| MGI-R182V | SEQ ID NO.: 17 | 617 |
| MGI-F187G | SEQ ID NO.: 19 | 195 |
| MGI-F187S | SEQ ID NO.: 18 | 261 |
| MGI-F187A | SEQ ID NO.: 21 | 255 |
| MGI-F187P | SEQ ID NO.: 20 | 325 |
| MGI-T299I | SEQ ID NO.: 23 | 250 |
| MGI-T299Y | SEQ ID NO.: 24 | 254 |
| MGI-T299C | SEQ ID NO.: 25 | 468 |
| MGI-T299M | SEQ ID NO.: 26 | 272 |
| MGI-T299Q | SEQ ID NO.: 22 | 286 |
| MGI-T299E | SEQ ID NO.: 27 | 338 |
| MGI-2 | SEQ ID NO.: 28 | 470 |
| MGI-2AQ | SEQ ID NO.: 29 | 195 |
| MGI-2FQ | SEQ ID NO.: 30 | 260 |
| MGI-3 | SEQ ID NO.: 31 | 512 |
| MGI-4 | SEQ ID NO.: 32 | 751 |

Example 13

Conversion of D-glucose to Fructose

The measurement was based on Kaneko et. al., (*Biosci Biotechnol Biochem.* 2000, 64:940-7) with modifications. Substrate solution B stock containing 50%(w/v) D-glucose, 20 mM sodium phosphate buffer (pH 6.5), 250 µM $CoCl_2$ (final concentration) and 5 mM $MgCl_2$ (final concentration) was adjusted to pH 6.5. Sixty µl of the substrate solution B was mixed with 40 µl of glucose isomerase mutant MGI-4 prepared as described in Example 10, incubated at 80° C. for 4 h and 100 µl of 20% trichloroacetic acid was added to stop the reaction. Ten µl of the supernatant, collected by centrifugation at 17,800 g for 15 minutes at 10° C., was diluted 100 fold and applied to high pressure liquid chromatography (HPLC) column µBNONDAPAK $NH_2$ SS COL 3.9×300 (Waters, Calif., USA) equipped with detector ELSD 500. The mobile phase acetonitrile:water (85:15) was run at a flow rate of 0.5 ml/min. The volume of the sample loaded was 10 µl.

FIG. 2 shows the results of the conversion of D-glucose to fructose by glucose isomerase mutant MGI-4 at 80° C.

Example 14

Thermostability of Wild-Type Glucose Isomerase

Two hundred μl of the partially purified glucose isomerase obtained as described in Example 9 were added to each of seven microfuge tubes, overlaid with 200 μl mineral oil, and placed in a 80° C. water bath. One of the seven tubes was removed from the water bath at a time 0 h, 2 h, 4 h, 8 h, 16 h, 32 h and 72 h, and centrifuged at 17,800 g for 15 minutes at 10° C. The residual protein and the glucose isomerase activity of the supernatants were determined as described in Example 11. FIG. 3 shows the thermostability of wild-type glucose isomerase at 80° C.

Example 15

Thermostability of Glucose Isomerase Mutants

The thermostability of glucose isomerase mutants MGI-2, MGI-3 and MGI-4, measured as described in Example 14, was shown on FIG. 3. As the figure indicates, the activity half-life of wild-type glucose isomerase at 80° C. was 4 hours, the activity half-life of MGI-2 at 80° C. was 4.4 hours, the activity half-life of MGI-3 at 80° C. was 21 hours, and the activity half-life of MGI-4 at 80° C. was 25.5 hours.

Example 16

The Effect of pH on Wild-Type Glucose Isomerase

Substrate solution C stock containing 1.0 M D-glucose, 20 mM sodium acetate buffer (pH 4.0), 250 μM $CoCl_2$ (final concentration) and 5 mM $MgCl_2$ (final concentration) was adjusted to pH 4.0; Substrate solution D stock containing 1.0 M D-glucose, 20 mM sodium acetate buffer (pH 4.5), 250 μM $CoCl_2$ (final concentration) and 5 mM $MgCl_2$ (final concentration) was adjusted to pH 4.5; Substrate solution E stock containing 1.0 M D-glucose, 20 mM sodium acetate buffer (pH 5.0), 250 μM $CoCl_2$ (final concentration) and 5 mM $MgCl_2$ (final concentration) was adjusted to pH 5.0; Substrate solution F stock containing 1.0 M D-glucose, 20 mM sodium acetate buffer (pH 5.5), 250 μM $CoCl_2$ (final concentration) and 5 mM $MgCl_2$ (final concentration) was adjusted to pH 5.5; Substrate solution G stock containing 1.0 M D-glucose, 20 mM sodium phosphate buffer (pH 6.0), 250 μM $CoCl_2$ (final concentration) and 5 mM $MgCl_2$ (final concentration) was adjusted to pH 6.0; Substrate solution H stock containing 1.0 M D-glucose, 20 mM sodium phosphate buffer (pH 6.5), 250 μM $CoCl_2$ (final concentration) and 5 mM $MgCl_2$ (final concentration) was adjusted to pH 6.5; Substrate solution I stock containing 1.0 M D-glucose, 20 mM sodium phosphate buffer (pH 7.0), 250 μM $CoCl_2$ (final concentration) and 5 mM $MgCl_2$ (final concentration) was adjusted to pH 7.0; Substrate solution J stock containing 1.0 M D-glucose, 20 mM sodium phosphate buffer (pH 7.5), 250 μM $CoCl_2$ (final concentration) and 5 mM $MgCl_2$ (final concentration) was adjusted to pH 7.5; Substrate solution K stock containing 1.0 M D-glucose, 20 mM sodium phosphate buffer (pH 8.0), 250 μM $CoCl_2$ (final concentration) and 5 mM $MgCl_2$ (final concentration) was adjusted to pH 8.0; Substrate solution L stock containing 1.0 M D-glucose, 20 mM Tris-HCL buffer (pH 8.5), 250 μM $CoCl_2$ (final concentration) and 5 mM $MgCl_2$ (final concentration) was adjusted to pH 8.5; and Substrate solution M stock containing 1.0 M D-glucose, 20 mM Tris-HCl buffer (pH 9.0), 250 μM $CoCl_2$ (final concentration) and 5 mM $MgCl_2$ (final concentration) was adjusted to pH 9.0. Eleven reaction mixtures each contained 10 μl of the glucose isomerase prepared as described in Example 9 and 90 μl of the stock solution C, D, E, F, G, H, I, J, K, L, or M were incubated at 80° C. for 10 minutes and quenched on ice immediately. The resultant fructose was measured as described in Example 11. FIG. 4 shows the pH effects on the wild-type glucose isomerase.

Example 17

The Effect of pH on Glucose Isomerase Mutants

The effect of pH on glucose isomerase mutants MGI-2, MGI-3 and MGI-4, measured as described in Example 16, was shown on FIG. 4. As the figure indicates, taking the activity of wild-type glucose isomerase under its optimal pH (pH 7.0) as 100%, glucose isomerase mutants MGI-2, MGI-3 and MGI-4 all maintained highly active in the pH range of 5.0 to 9.0. At pH 5.0 the relative activity of MGI-2 was 365%, 72% of the activity under its optimal pH (pH 7.0). At pH 5.0 the relative activity of MGI-3 was 370%, 70% of the activity under its optimal pH (pH 7.0). At pH 5.0 the relative activity of MGI-4 was 600%, 80% of the activity under its optimal pH (pH 7.0).

Example 18

Measurement of Kinetic Parameters of Wild-Type Glucose Isomerase

Substrate solution N stock containing phosphate-$MgCl_2$—$CoCl_2$ buffer (20 mM sodium phosphate [pH 6.5], 250 μM $CoCl_2$ and 5 mM $MgCl_2$) and 2.0 M D-glucose was adjusted to pH 6.5. The phosphate-$MgCl_2$—$CoCl_2$ buffer was used to dilute the substrate solution N into solutions containing 1.8 M, 1.6 M, 1.4 M, 1.2 M, 1.0 M, 0.8 M, 0.6 M, 0.4 M, 0.2 M, 0.1 M, 0.05 M or 0.025 M D-glucose. Thirteen reaction mixtures, each contained 10 μl partially purified wild-type glucose isomerase as described in Example 9 and 90 μl of the substrate solution N of different D-glucose concentrations, were incubated at 65° C. or 80° C. for 10 minutes, and the resultant fructose was determined as described at Example 11. Applying Michaelis-Menten equation and Lineweaver-Burk plot, the $k_m$, $V_{max}$ and $K_{cat}$ were determined from the data and listed in Table 3.

Example 19

Measurement of Kinetic Parameters of Glucose Isomerase Mutant MGI-4

The kinetic parameters of glucose isomerase mutant MGI-4 were measured as described in Example 18 and listed in Table 3, which compares the kinetic parameters of wild-type glucose isomerase and mutant MGI-4.

TABLE 3

Kinetic Parameters of Wild-type Glucose Isomerase (wild-type) and Glucose Isomerase Mutant MGI-4 (MGI-4)

| Sub- | $K_m$ (mM) | | Kcat (min$^{-1}$) | | Kcat/Km (mM$^{-1}$ min$^{-1}$) | |
|---|---|---|---|---|---|---|
| strate | Wild-type | MGI-4 | Wild-type | MGI-4 | Wild-type | MGI-4 |
| 65° C. | | | | | | |
| D-glucose | 138.5 | 27.9 | 344.5 | 1009.0 | 2.50 | 36.1 |
| 80° C. | | | | | | |
| D-glucose | 149.4 | 51.3 | 881.1 | 2981.1 | 5.90 | 58.1 |

Example 20

Immobilization of Glucose Isomerase Mutant MGI-4

The immobilization procedure was based on Ge et al., (*Appl. Biochem. Biotechnol.* 69:57-69, 1998). One hundred grams of the immobilization carrier trimethylamine polystyrene hydrochloride, provided by Chengdu Institute of Chemical Industry, was mixed with 8 grams of partially purified glucose isomerase mutant MGI-4 prepared as described in Example 10 in 1 liter of 10 mM phosphate buffer (pH 8.0), and stirred (60-120 rpm/minute) at room temperature (22° C.) for 18 hours. The resultant immobilized enzyme was collected by filtration and washed with water three times. The total immobilized enzyme generated was 170 grams. The activity of the immobilized enzyme, measured as described in Example 11 using 0.01 gram of the immobilized enzyme, was 820 units/gram.

Example 21

Immobilization of *E. coli* Cells Carrying Glucose Isomerase Mutant MGI-4

*E. coli* HB101 cells carrying pGEMT-MGI-4 was grown in LB broth containing 50 mg ampicillin/L to $OD_{600}$ of 7. Ten grams of the cells, collected by centrifugation, were mixed well with 20 mL of 3% sodium alginate, and squeezed through a needle of 0.5 mm in diameter into 500 ml of 2% NaCl solution. The mixture was allowed to react for 1 hour at room temperature and washed three times by soaking in distilled water, each time for half an hour. The resultant immobilized cells of approximate 30 grams were measured for glucose isomerase activity as described in Example 11 using 0.01 gram of the immobilized cells. The activity was 370 units/gram.

The scope of protection of the invention is not limited by the detailed description provided in the above Examples. Various modifications and variations can be made by those skilled in the field and these modifications and variations are within the scope of the invention if they fall within the scope of protection as defined by the Claims.

---

What is claimed is:

1. An isolated glucose isomerase mutant comprising SEQ ID NO: 2 having a mutation at position 187 of SEQ ID NO: 2, and having 50% higher specific glucose isomerase activity towards D-glucose than the wild type glucose isomerase.

2. The glucose isomerase mutant of claim 1, wherein phenylalanine at position 187 is substituted with glycine, serine, alanine or proline.

3. An isolated glucose isomerase mutant comprising SEQ ID NO: 4, wherein the Xaa at position 187 is glycine, serine, alanine or proline.

4. The glucose isomerase mutant of claim 3, wherein the Xaa at position 187 is proline.

5. The glucose isomerase mutant of claim 1, wherein the mutant further comprises a mutation selected from the group consisting of position 139, 182 and 299, wherein the substitution of the tryptophan at position 139 is with any other natural amino acid, the substitution of the arginine at position 182 with any other natural amino acid, and the substitution of threonine at position 299 the with any other natural amino acid.

6. The glucose isomerase mutant of claim 5, wherein the phenylalanine at position 187 is substituted with glycine, serine, alanine or proline.

7. The glucose isomerase mutant of claim 5, wherein threonine at position 299 is substituted with isoleucine, tyrosine, cysteine, methionine, glutamic acid or glutamine.

8. The glucose isomerase mutant of claim 5, wherein the mutant has at least three mutations selected from the group consisting of substitution of tryptophan at position 139 with any other natural amino acid, substitution of arginine at position 182 with any other natural amino acid, the phenylalanine at position 187 with any other natural amino acid and substitution of threonine at position 299 with any other natural amino acid.

9. The glucose isomerase mutant of claim 8, wherein arginine at position 182 is substituted with proline, serine, alanine, isoleucine, threonine or valine.

10. The glucose isomerase mutant of claim 8, wherein phenylalanine at position 187 is substituted with glycine, serine, alanine or proline.

11. The glucose isomerase mutant of claim 8, wherein threonine at position 299 substituted with isoleucine, tyrosine, cysteine, methionine, glutamic acid or glutamine.

12. The glucose isomerase mutant of claim 8, wherein tryptophan at position 139 is substituted with any other natural amino acid, arginine at position 182 is substituted with any other natural amino acid, phenylalanine at position 187 is substituted with any other natural amino acid and the threonine at position 299 is substituted with any other natural amino acid.

13. The glucose isomerase mutant of claim 12, wherein arginine at position 182 is substituted with to proline, serine, alanine, isoleucine, threonine or valine.

14. The glucose isomerase mutant of claim 12, wherein phenylalanine at position 187 is substituted with glycine, serine, alanine or proline.

15. The glucose isomerase mutant of claim 12, wherein threonine at position 299 is substituted with isoleucine, tyrosine, cysteine, methionine, glutamic acid, glutamine.

16. An isolated glucose isomerase mutant comprising SEQ ID NO: 4 wherein Xaa at position 139 is phenylalanine, Xaa at position 182 is alanine, Xaa at position 187 is serine and Xaa at position 299 is glutamine.

17. A method for conversion of D-glucose to fructose syrup by contacting the glucose isomerase mutant as claimed in claim 1.

18. The method of claim 17, wherein said fructose syrup contains at least 55 wt % fructose.

* * * * *

UNITED STATES PATENT AND TRADEMARK OFFICE
CERTIFICATE OF CORRECTION

| | | |
|---|---|---|
| PATENT NO. | : 7,919,300 B2 | Page 1 of 1 |
| APPLICATION NO. | : 11/597609 | |
| DATED | : April 5, 2011 | |
| INVENTOR(S) | : Jun Wang et al. | |

It is certified that error appears in the above-identified patent and that said Letters Patent is hereby corrected as shown below:

IN THE CLAIMS:

Column 105, Claim 5, Line 29
Please delete "position 299 the with any other natural amino"
and replace with -- position 299 with any other natural amino --

Column 106, Claim 12, Lines 23-24
Please delete "any other natural amino acid and the threonine at position 299"
and replace with -- any other natural amino acid and threonine at position 299 --

Column 106, Claim 13, Line 27
Please delete "position 182 is substituted with to proline"
and replace with -- position 182 is substituted with proline --

Signed and Sealed this
Seventh Day of June, 2011

David J. Kappos
*Director of the United States Patent and Trademark Office*